(12) United States Patent
Mailliet et al.

(10) Patent No.: US 6,887,873 B2
(45) Date of Patent: May 3, 2005

(54) TRIAZINE DERIVATIVES AND THEIR APPLICATION AS ANTITELOMERASE AGENTS

(75) Inventors: Patrick Mailliet, Fontenay sous Bois (FR); Abdelazize Laoui, Bridgewater, NJ (US); Jean-François Riou, Reims (FR); Gilles Doerflinger, Les Ulis (FR); Jean-Louis Mergny, Villejuif (FR); François Hamy, Illzach (FR); Thomas Caulfield, Paris (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 10/103,883

(22) Filed: Mar. 25, 2002

(65) Prior Publication Data

US 2003/0087931 A1 May 8, 2003

Related U.S. Application Data

(60) Provisional application No. 60/332,009, filed on Nov. 23, 2001.

(30) Foreign Application Priority Data

Mar. 23, 2001 (FR) .............................. 01 03916
Aug. 2, 2001 (FR) .............................. 01 10370

(51) Int. Cl.$^7$ ...................... C07D 401/14; A61K 31/53
(52) U.S. Cl. ...................... 514/245; 544/198; 544/209
(58) Field of Search .......................... 514/245; 540/198, 540/209

(56) References Cited

U.S. PATENT DOCUMENTS 5,854,244 A 12/1998 Jarman et al.
6,262,053 B1 7/2001 Uckun et al.

FOREIGN PATENT DOCUMENTS

| JP | 11-60573 | 3/1999 |
| WO | WO 99/40087 | 8/1999 |
| WO | WO 01/40218 A1 | 6/2001 |

OTHER PUBLICATIONS

Chen et al., Spectroscopic Recognition of Guanine Dimeric Hairpin Quadruplexes by a Carbocyanine Dye, *Proc. Natl. Acad. Sci. USA*, 93: 2635–2639, 1996.
Kreutzberger et al., Synthesis and Spectroscopic Analyses of Dianilinotriazines, *Chemiker–Zeitung*, 114: 208–210, 1990. (English–language translation provided.).
Sun, et al., Inhibition of Human Telomerase by a G–Quadruplex–Interactive Compound, *Journal of Medicinal Chemistry*, 40: 2113–2116, 1997.
Wheelhouse et al., Cationic Porphyrins as Telomerase Inhibitors: The Interaction of Tetra–(N–methyl–4–pyridy) Porphine with Quadruplex DNA, *J. Am. Chem. Soc.*, 120: 3261–3262, 1998.

*Primary Examiner*—Thomas C. McKenzie
(74) *Attorney, Agent, or Firm*—Balaran Gupta

(57) ABSTRACT

The present invention relates to cancer therapy and to novel anticancer agents having a mechanism of action which is quite specific. It also relates to novel chemical compounds as well as their therapeutic application in humans.

34 Claims, No Drawings

TRIAZINE DERIVATIVES AND THEIR APPLICATION AS ANTITELOMERASE AGENTS

This application claims priority to French Application No. 0103916, filed Mar. 23, 2001, and French Application No. 0110370, filed Aug. 2, 2001, and claims the benefit of U.S. Provisional Application No. 60/332,009, filed Nov. 23, 2001, each of which are herein incorporated by reference.

The present invention relates to cancer therapy and to novel anticancer agents having a mechanism of action which is quite specific. It also relates to novel chemical compounds as well as their therapeutic application in humans.

The present invention relates to the use of novel non-nucleotide chemical compounds which interact with specific structures of deoxyribonucleic acid (DNA) or ribonucleic acid (RNA). These novel compounds consist of a distribution agent linked to two aminoaromatic groups. These novel compounds are useful in the treatment of cancers and act in particular as telomerease-inhibiting agents. They are particularly useful for stabilizing DNA in G-quadruplex structure (guanine tetrads). The therapeutic application of the inhibition of telomerease via the stabilization of these G-quadruplexes is the termination of cellular mitosis and the death of rapidly dividing cells such as cancer cells and possibly the induction of the senescence of cancer cells.

The compounds of the present invention have the advantage, from the therapeutic point of view, of blocking telomerease. From a biological point of view, telomerease allows the addition of repetitive DNA sequences of the T T A G G G type, termed telomereic sequences, at the end of the telomere, during cell division. Through this action, telomerease renders the cell immortal. Indeed, in the absence of this enzymatic activity, the cell loses, at each division, 100 to 150 bases, which rapidly renders it senescent. During the appearance of rapidly dividing cancer cells, it appeared that these cells possessed telomeres which were maintained at a stable length during cell division. In these cancer cells, it appeared that telomerease was highly activated and that it allowed the addition of repetitive motifs of telomereic sequences at the end of the telomere and therefore allowed conservation of the length of the telomere in the cancer cells. It appeared for some time that more than 85% of cancer cells showed positive tests for the presence of telomerease whereas somatic cells do not show this characteristic.

Thus, telomerease is a highly coveted target for treating cancer cells. The first obvious approach for blocking telomerease was the use of nucleotide structures (Chen et al., Proc. Natl. Acad. Sci. USA 93(7), 2635–2639). Among the non-nucleotide compounds which have been used in the prior art, there may be mentioned the diaminoanthraquinones (Sun et al., J. Med. Chem. 40(14), 2113–6) or the diethyloxadicarbocyanins (Wheelhouse R. T. et al., J. Am. Chem. Soc. 1998(120), 3261–2).

Patent WO 99/40087 describes the use of compounds which interact with the G-quadruplex structures which are perylene compounds and carbocyanins containing at least seven rings including two heterocycles.

It appeared, quite surprisingly, that simple structures made it possible to obtain a result which is at least equivalent with structures which are a lot less complicated from a chemical point of view. The compounds of the present invention which meet the intended objective, that is to say which bind the G-quadruplex structure of DNA or of RNA and in particular the G-quadruplex structure of the telomeres and thereby exhibit a telomerease-inhibiting activity, correspond to the following general formula:

nitrogen-containing aromatic ring—$NR_3$—distribution agent—$NR'_3$—aromatic ring in which the nitrogen-containing aromatic ring represents:
   a quinoline or isoquinoline optionally substituted with at least one radical chosen from a group N(Ra)(Rb) in which Ra and Rb, which are identical or different, represent hydrogen or a C1–C4 alkyl radical, and a short-chain C1–C4 alkoxy or alkyl group or
   a quinoline or isoquinoline possessing a nitrogen atom in quaternary form or
   a benzamidine or
   a pyridine the aromatic ring represents
   a quinoline optionally substituted with at least one radical chosen from a group N(Ra)(Rb) in which Ra and Rb, which are identical or different, represent hydrogen or a C1–C4 alkyl radical, and a short-chain C1–C4 alkoxy or alkyl group or
   a quinoline possessing a nitrogen atom in quaternary form or
   a benzamidine or
   a pyridine or
   a phenyl ring optionally substituted with a halogen group; C1–C4 alkoxy group; cyano group; carbonylamino group optionally substituted with one or more C1–C4 alkyl groups; guanyl group; C1–C4 alkylthio group; amino group, C1–C4 alkylamino group, C1–C4 dialkylamino group for each alkyl group and in which the alkyl portions may together form a C3–C8 ring, nitro group; C1–C4 alkyleneamino group; C2–C4 alkenyleneamino group;
   a mono- or bi- or tricyclic heterocyclic ring comprising 0 to 2 heteroatoms per ring provided that at least one heteroatom is present in at least one ring optionally substituted with one or more C1–C4 alkyl groups or with C1–C4 alkylene or C2–C4 alkenylene groups R3 and R'3, which are identical or different, represent independently of one another hydrogen or a C1–C4 alkyl radical the distribution agent represents:
   a triazine group optionally substituted with an aromatic ring as defined above or with a radical XR1(R2) in which X represents a nitrogen atom N to form NR1R2, a linear or branched C1–C6 alkyl radical to form alkR1R2, an oxygen atom O to form OR1 or a sulphur atom S to form SR1, with R1 and R2, which are identical or different, are chosen from a hydrogen atom; a C1–C8 alkyl radical optionally substituted with one or more radicals which are identical or different; an aromatic ring as defined above; a quinuclidine radical; a pyrrolidinyl radical which is itself optionally substituted with an alkyl or phenylalkyl radical with alkyl as C1–C4; a piperazinyl radical which is itself optionally substituted with an alkyl, cycloalkyl or phenylalkyl radical; a morpholinyl radical; a pyridyl radical or a piperidyl radical which are optionally substituted with one or more alkyl or phenylalkyl radicals with alkyl C1–C4; an indazolyl radical; a naphthyl radical; a benzotriazole radical; a pyrimidinyl radical optionally substituted with one or more alkyls with alkyl as C1–C4; an acenaphthene radical, it being understood that, when XR1R2 represents NR1R2, then R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a saturated or unsaturated 3- to 6-membered monocyclic or 8- to 10-membered bicyclic radical optionally containing one or two heteroatoms, which are identical or different, chosen from N, O or S, a diazine group optionally substituted with the same groups as the triazine or one of its salts, these compounds being in all the possible isomeric forms, racemates, enantiomers and diastereoisomers.

Among the compounds defined above, there may be mentioned the compounds characterized in that, when one or both of R1 and R2 represents (represent) a C1–C8 alkyl radical optionally substituted with one or more radicals which are identical or different, these radicals are chosen from the amino radical which is itself optionally substituted with one or two radicals which are identical or different, chosen from alkyl, hydroxyalkyl, alkoxyalkyl, phenylalkyl, carboxyalkyl, hydroxycarboxyalkyl, acyl, naphthyl, phenyl and alkylphenyl radicals; trialkylammonio radical; hydroxyl radical; C1–C4 alkoxy radical; thioalkoxy radical; trifluoromethyl radical; free, salified, esterified or amidated carboxyl radical; pyrrolidinyl radical optionally substituted with C1–C4 alkyl; piperidyl radical; piperazinyl radical optionally substituted with alkyl or phenylalkyl with alkyl as C1–C4; morpholinyl radical; pyridyl radical; naphthyl radical or phenyl radical itself optionally substituted with one or more radicals chosen from C1–C4 alkoxy radicals, halogen or amino radical optionally substituted as defined above.

Among the compounds defined above, there may be mentioned in particular the compounds characterized in that the distribution agent represents:

a triazine group optionally substituted with an aromatic ring as defined above or with a radical XR1(R2) in which X represents a nitrogen atom N to form NR1R2, a linear or branched C1–C6 alkyl radical to form alkR1R2, an oxygen atom O to form OR1 or a sulphur atom S to form SR1, with R1 and R2, which are identical or different, are chosen from a hydrogen atom; C1–C8 alkyl optionally substituted with one or more radicals chosen from the radicals amino, alkylamino, dialkylamino, dialkoxyalkylamino, dihydroxyalkylamino, alkoxyalkylamino, hydroxyalkylamino, hydroxycarboxyalkylamino, trialkylamino+, naphthylamino, phenylamino, acylamino, (alkyl)(phenylalkyl)amino, (phenyl)(alkyl)amino, (alkylphenyl)(alkyl)amino, hydroxyl, C1–C4 alkoxy, C1–C4 thioalkoxy, trifluoromethyl, free, salified, esterified or amidated carboxyl, pyrrolidinyl optionally substituted with C1–C4 alkyl, piperidyl, piperazinyl optionally substituted with alkyl or phenylalkyl with alkyl as C1–C4, morpholinyl, pyridyl, naphthyl or phenyl optionally substituted with one or more radicals chosen from the radicals C1–C4 alkoxy, halogen, amino, alkylamino and dialkylamino; an aromatic ring as defined above; a quinuclidine radical; a pyrrolidinyl radical which is itself optionally substituted with an alkyl or phenylalkyl radical with alkyl as C1–C4; a piperazinyl radical which is itself optionally substituted with an alkyl, cycloalkyl or phenylalkyl radical; a morpholinyl radical; a pyridyl radical or a piperidyl radical which are optionally substituted with one or more alkyl or phenylalkyl radicals with alkyl C1–C4;

an indazolyl radical; a naphthyl radical, a benzotriazole radical; a pyrimidinyl radical optionally substituted with one or more alkyls with alkyl as C1–C4; an acenaphthene radical, it being understood that, when XR1R2 represents NR1R2, then R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a radical chosen from the following radicals: piperazinyl optionally substituted with one or more radicals which are identical or different; pyrrolidinyl optionally substituted with C1–C4 alkyl or alkoxy, hydroxyl, acylamino, pyrrolidinylalkyl and pyridyl; 1,2,3,4-tetrahydroisoquinolinyl; diazepine optionally substituted with alkyl or pyrrolidinylalkyl; piperidyl optionally substituted with alkyl, alkoxy or alkoxyalkyl, hydroxyl and cycloalkylalkyl; morpholinyl; imidazolinyl optionally substituted with alkyl, or a diazine group optionally substituted with the same groups as the triazine or one of its salts, these compounds being in all the possible isomeric forms, racemates, enantiomers and diastereoisomers.

Among the compounds defined above, there may be mentioned the compounds characterized in that XR1(R2) is such that, when X represents N, either one of R1 and R2 represents a hydrogen atom or a C1–C4 alkyl radical optionally substituted with an amino, alkylamino, dialkylamino or phenyl radical and the other of R1 and R2 is chosen from the values defined for R1 and R2 in any one of Claims 1 to 8 or R1 and R2 together form with the nitrogen atom to which they are attached a piperazinyl radical optionally substituted with one or more radicals chosen from alkyl, aminoalkyl, alkylaminoalkyl, dialkylaminoalkyl, phenylalkyl, alkoxyalkyl, hydroxyalkyl, hydroxyalkoxyalkyl with alkoxy, pyrrolidinylalkyl, C3–C8 cycloalkyl, pyrazinyl, pyrimidinyl, pyridyl, furylcarbonyl, furfurycarbonyl, quinolyl; pyrrolidinyl optionally substituted with C1–C4 alkyl or alkoxy, hydroxyl, acylamino, pyrrolidinylalkyl and pyridyl; 1,2,3,4-tetrahydroisoquinolinyl; diazepine optionally substituted with alkyl or pyrrolidinylalkyl; piperidyl optionally substituted with alkyl, alkoxy or alkoxyalkyl, hydroxyl and cycloalkylalkyl; morpholinyl; imidazolinyl optionally substituted with alkyl.

The subject of the present invention is the compounds which bind the G-quadruplex structure of the telomeres characterized in that they correspond to the general formula as defined above.

The present invention thus relates to compounds as defined above characterized in that they correspond to the following general formula:

nitrogen-containing aromatic ring—NR$_3$—distribution agent—NR'$_3$—aromatic ring in which the nitrogen-containing aromatic ring represents:

a quinoline optionally substituted with at least one group N(Ra)(Rb) in which Ra and Rb, which are identical or different, represent hydrogen or a C1–C4 alkyl radical, (or) a short-chain C1–C4 alkoxy or alkyl group or a quinoline possessing a nitrogen atom in quaternary form or a benzamidine or
a pyridine
the aromatic ring represents
  a quinoline optionally substituted with at least one group N(Ra)(Rb) in which Ra and Rb, which are identical or different, represent hydrogen or a C1–C4 alkyl radical, (or) a short-chain C1–C4 alkoxy or alkyl group or
  a quinoline possessing a nitrogen atom in quaternary form or
  a benzamidine or
  a pyridine or
  a phenyl ring optionally substituted with a halogen group; C1–C4 alkoxy group; cyano group; carbonylamino group optionally substituted with one or more C1–C4 alkyl groups; guanyl group; C1–C4 alkylthio group; amino group, C1–C4 alkylamino group, C1–C4 dialkylamino group for each alkyl group and in which the alkyl portions may together form a C3–C8 ring, nitro group; C1–C4 alkyleneamino group; C2–C4 alkenyleneamino group,
  a mono- or bi- or tricyclic heterocyclic ring comprising 0 to 2 heteroatoms per ring provided that at least one heteroatom is present in at least one ring optionally substituted with one or more C1–C4 alkyl groups or with C1–C4 alkylene or C2–C4 alkenylene groups
R3 and R'3, which are identical or different, represent independently of one another hydrogen or a C1–C4 alkyl radical
the distribution agent represents:
  a triazine group optionally substituted with a radical XR1(R2) in which X represents a nitrogen atom N to form NR1R2, a linear or branched C1–C6 alkyl radical to form alkR1R2, an oxygen atom O to form OR1 or a sulphur atom S to form SR1,
  with R1 and R2, which are identical or different, are chosen from a hydrogen atom; C1–C8 alkyl optionally substituted with a radical amino, alkylamino, dialkylamino, (phenyl)(alkyl)amino, (alkylphenyl)(alkyl)amino, C1–C4 alkoxy, C1–C4 thioalkoxy, trifluoromethyl, pyrrolidinyl, piperidyl, piperazinyl, morpholinyl, pyridyl or phenyl; an aromatic ring as defined above; a quinuclidine radical, a radical pyrrolidinyl, piperazinyl, morpholinyl, pyridyl or a piperidyl radical optionally substituted with C1–C4 alkyl it being understood that R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a saturated or unsaturated 3- to 6-membered monocyclic or 8- to 10-membered bicyclic radical optionally containing one or two heteroatoms, which are identical or different, chosen from N, O or S,
  a diazine group optionally substituted with the same groups as the triazine
or one of its salts,
these compounds being in all the possible isomeric forms, racemates, enantiomers and diastereoisomers.

For the purposes of the above formula, nitrogen-containing aromatic ring is understood to mean a heterocycle comprising at least one nitrogen atom or an aromatic group containing no heteroatom in the ring but containing at least one nitrogen atom in a hydrocarbon chain attached to the ring, such as for example a guanidino or guanyl chain.

The aromatic ring represents in particular a quinaldine, quinoline, benzamidine, pyridine and phenyl radical as defined above and optionally substituted as indicated above.

As C3–C8 ring which the alkyl portions of the dialkylamino radicals defined above can form, there may be mentioned for example aziriridine, azetidine, pyrrolidine, oxazolidine, thiazolidine, piperidine, piperazine, morpholine, thiomorpholine or azepine rings.

In the products above and below, the chemical radicals have their customary meanings which are found in the documents used by persons skilled in the art and correspond in particular to the following definitions:
  the term alkyl radical denotes linear or branched radicals, in particular methyl, ethyl, propyl, isopropyl, butyl, isobutyl, sec-butyl, tert-butyl, pentyl, isopentyl, hexyl, isohexyl and also heptyl, octyl, nonyl and decyl radicals and their linear or branched position isomers,
  the term alkoxy radical denotes linear or branched radicals, in particular methoxy, ethoxy, propoxy, isopropoxy, linear, secondary or tertiary butoxy, pentoxy or hexoxy radicals and their linear or branched position isomers,
  the term halogen atom denotes chlorine, fluorine, bromine or iodine, and in particular chlorine and fluorine, atoms
  the term cycloalkyl radical denotes cyclohexyl, cyclopropyl, cyclobutyl and also cycloheptyl and cyclooctyl radicals
  the term alkylphenyl denotes a phenyl radical substituted with one or more linear or branched alkyl radicals as defined above, preferably containing at most 4 carbon atoms
  the terms NH(alk) and N(alk)(alk) denote an amino radical substituted with one or two alkyl radicals, respectively, such alkyl radicals being linear or branched and preferably containing at most 4 carbon atoms
  the term acylamino denotes —C(O)—NH2, —C(O)—NH(alk) and —C(O)—N(alk)(alk) radicals in which the NH(alk) and N(alk)(alk) radicals have the meaning indicated above
  the term acyl denotes an R—C(O)— radical in which R represents a radical chosen from a hydrogen atom, linear or branched alkyl radicals containing at most 8 carbon atoms or a saturated or unsaturated carbocyclic or heterocyclic radical, chosen for example from the aromatic or nonaromatic rings defined above: the term acyl thus denotes for example formyl, acetyl, propionyl, butanoyl, pentanoyl, hexanoyl, benzoyl, pyrrolidinylcarbonyl, pyrazinylcarbonyl, piperazinylcarbonyl, furylcarbonyl or furfurylcarbonyl radicals.

The carboxyl radical(s) of the products of formula (I) may be salified or esterified with various groups known to persons skilled in the art among which there may be mentioned, for example:
  among the salifying compounds, inorganic bases such as, for example, a sodium, potassium, lithium, calcium, magnesium or ammonium equivalent or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, N-methylglucamine,
  among the esterifying compounds, alkyl radicals in order to form alkoxycarbonyl groups such as, for example, methoxycarbonyl, ethoxycarbonyl, tert-butoxycarbonyl or benzyloxycarbonyl, it being possible for these alkyl radicals to be substituted with radicals chosen for example from halogen atoms, hydroxyl, alkoxy, acyl, acyloxy, alkylthio, amino or aryl radicals as, for example, in chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may be, for example, the salts formed with hydrochloric, hydrobromic, hydriodic, nitric, sulphuric, phosphoric, propionic, acetic, trifluoroacetic, formic, benzoic, maleic, fumaric, succinic, tartaric, citric, oxalic, glyoxylic, aspartic and ascorbic acids, alkylmonosulphonic acids such as for example methanesulphonic acid, ethanesulphonic acid, propanesulphonic acid, alkyldisulphonic acids such as, for example, methanedisulphonic acid, alpha, beta-ethanedisulphonic acid, arylmonosulphonic acids such as benzenesulphonic acid and aryldisulphonic acids.

The pharmaceutically acceptable salts of the products of formula (I) are in particular utilizable nontoxic salts: such salts of the products of formula (I) as defined above may be obtained by ordinary methods known to persons skilled in the art, for example by combining a compound of formula (I) with an organic or inorganic acid or a base in a solvent or a dispersant or from another salt by exchange of cation or anion.

It may be restated that the stereoisomerism may be defined within its broad term as the isomerism of compounds having the same structural formula, but in which the various groups are arranged differently in space, as in particular in monosubstituted cyclohexanes in which the substituent may be in the axial or equatorial position, and the various possible rotational conformations of the ethane derivatives. Nevertheless, there is another type of stereoisomerism, due to the different spatial arrangements of substituents attached, either to double bonds, or to rings, which is often called geometric isomerism or cis-trans isomerism. The term stereoisomers is used in the present application in its broadest sense and therefore covers all the compounds indicated above.

The subject of the present invention is in particular the compounds as defined above, characterized in that the distribution agent represents:

a triazine group optionally substituted with a radical XR1(R2) in which X represents a nitrogen atom N in order to form NR1R2, an oxygen atom O in order to form OR1 or a sulphur atom S in order to form SR1, with R1 and R2, which are identical or different, are chosen from a hydrogen atom; C1–C8 alkyl optionally substituted with a radical amino, alkylamino, dialkylamino, (phenyl)(alkyl)amino, (alkylphenyl)(alkyl)amino, C1–C4 alkoxy, with a radical pyrrolidinyl, pyridyl or with a phenyl radical; an aromatic ring as defined above; a quinuclidine radical, a pyrrolidinyl radical or a piperidyl radical optionally substituted with C1–C4 alkyl it being understood that R1 and R2, which are identical, both do not represent hydrogen or unsubstituted C1–C4 alkyl and R1 and R2, which are different, do not represent one hydrogen and the other unsubstituted C1–C4 alkyl, or alternatively, when X represents N, R1 and R2 together form with X to which they are attached a piperazinyl, piperidyl, pyrrolidinyl, morpholinyl or thiomorpholinyl radical, a diazine group optionally substituted with the same groups as the triazine or one of its salts, these compounds being in all the possible isomeric forms, racemates, enantiomers and diastereoisomers.

The subject of the present invention is particularly the compounds as defined above, characterized in that the diazine groups are pyrimidines or quinazolines.

The subject of the present invention is more particularly the compounds as defined above, characterized in that XR1(R2) is such that, when X represents N, either one of R1 and R2 represents a hydrogen atom and the other of R1 and R2 is chosen from the values defined for R1 and R2 or R1 and R2 together form with the nitrogen atom to which they are attached a piperazinyl, pyrrolidinyl, piperidyl or morpholino radical.

The present invention relates particularly to compounds as defined above, characterized in that they correspond to formula (I) below:

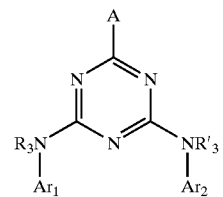

in which:

A represents a radical XR1(R2) in which X represents a nitrogen, oxygen, or sulphur atom or a C1–C6 alkyl radical in order to form one of the following radicals: NR1R2 with R1 and R2, which are identical or different, are chosen from a hydrogen atom; a C1–C8 alkyl optionally substituted with one or more radicals which are identical or different; an aromatic ring as defined above; a quinuclidine radical; a pyrrolidinyl radical which is itself optionally substituted with an alkyl or phenylalkyl radical with alkyl as C1–C4; a piperazinyl radical which is itself optionally substituted with an alkyl, cycloalkyl or phenylalkyl radical; a morpholinyl radical; a pyridyl radical or a piperidyl radical which is optionally substituted with one or more alkyl or phenylalkyl radicals with alkyl C1–C4; an indazolyl radical; a naphthyl radical; a benzotriazole radical; a pyrimidinyl radical optionally substituted with one or more alkyls with alkyl as C1–C4; an acenaphthene radical, it being understood that, when XR1R2 represents NR1R2, then R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a saturated or unsaturated 3- to 6-membered monocyclic or 8- to 10-membered bicyclic radical optionally containing one or two heteroatoms, which are identical or different, chosen from N, O or S, a group OR1 or SR1 in which R1 has the same meaning as above, it being understood that R1 does not represent hydrogen or unsubstituted C1–C4 alkyl, or an alkyl group containing from 1 to 6 carbon atoms, substituted with R1 R2 as defined above R3 and R'3, which are identical or different, represent independently of one another hydrogen or a C1–C4 alkyl group Ar₁ and Ar₂, which are identical or different, represent
when Ar₁ and Ar₂ are identical:
a quinoline motif optionally substituted with at least one group N(Ra)(Rb) in which Ra and Rb, which are identical or different, represent hydrogen or a C1–C4 alkyl radical, (or) a short-chain alkoxy or alkyl group containing 1 to 4 carbon atoms or
a quinoline possessing a nitrogen atom in quaternary form or
a benzamidine or
a pyridine attached at the 4-position or fused with an aryl or heteroaryl group optionally substituted with a C1–C4 alkyl group
when Ar₁ and Ar₂ are different
Ar₁ and Ar₂ both represent one of the possibilities mentioned above for Ar₁ and Ar₂ or
Ar₁ represents one of the above possibilities and Ar₂ represents
a phenyl ring optionally substituted with a halogen group, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group for each alkyl group, nitro group, C1–C4 alkyleneamino group, (or) C2–C4 alkenyleneamino group, or a piperazinyl radical optionally substituted with a C1–C4 alkyl radical,
a mono- or bi- or tricyclic heterocyclic ring comprising 0 to 2 heteroatoms per ring provided that at least one heteroatom is present in at least one ring optionally substituted with one or more C1–C4 alkyl groups or with C1–C4 alkylene or C2–C4 alkenylene groups
or one of its salts, these compounds of formula (I) being in all the possible isomeric forms, racemates, enantiomers and diastereoisomers.

The present invention relates in particular to the compounds as defined above characterized in that, when one or both of R1 and R2 represents (represent) a C1–C8 alkyl radical optionally substituted with one or more radicals which are identical or different, these radicals are chosen from the amino radical which is itself optionally substituted with one or two radicals which are identical or different, chosen from alkyl, hydroxyalkyl, alkoxyalkyl, phenylalkyl, carboxyalkyl, hydroxycarboxyalkyl, acyl, naphthyl, phenyl and alkylphenyl radicals; trialkylammonio radical; hydroxyl radical; alkoxy radical; thioalkoxy radical; trifluoromethyl radical; free, salified, esterified or amidated carboxyl radical; pyrrolidinyl radical optionally substituted with C1–C4 alkyl; piperidyl radical; piperazinyl radical optionally substituted with alkyl or phenylalkyl with alkyl as C1–C4; morpholinyl radical; pyridyl radical; naphthyl radical or phenyl radical itself optionally substituted with one or more radicals chosen from C1–C4 alkoxy radicals, halogen or amino radical optionally substituted as defined above.

The present invention thus relates to the compounds as defined above, characterized in that XR1(R2) is such that, when X represents N, either one of R1 and R2 represents a hydrogen atom and the other of R1 and R2 is chosen from the values defined for R1 and R2, or R1 and R2 together form with the nitrogen atom to which they are attached a piperazinyl, pyrrolidinyl, piperidyl, morpholinyl, thiomorpholinyl, imidazolinyl, diazepine or 1,2,3,4-tetrahydroisoquinoline radical, all these radicals being optionally substituted with one or more radicals.

The present invention relates in particular to the compounds as defined above, characterized in that A represents an aromatic ring as defined above or a radical XR1(R2) in which X represents a nitrogen atom N to form NR1R2, a linear or branched C1–C6 alkyl radical to form alkR1R2, an oxygen atom O to form OR1 or a sulphur atom S to form SR1, with R1 and R2, which are identical or different, are chosen from a hydrogen atom; C1–C8 alkyl optionally substituted with one or more radicals chosen from the radicals amino, alkylamino, dialkylamino, dialkoxyalkylamino, dihydroxyalkylamino, alkoxyalkylamino, hydroxyalkylamino, hydroxycarboxyalkylamino, trialkylammonio, naphthylamino, phenylamino, acylamino, (alkyl)(phenylalkyl)amino, (phenyl)(alkyl)amino, (alkylphenyl)(alkyl)amino, hydroxyl, C1–C4 alkoxy, C1–C4 thioalkoxy, trifluoromethyl, free, salified, esterified or amidated carboxyl, pyrrolidinyl optionally substituted with C1–C4 alkyl, piperidyl, piperazinyl optionally substituted with alkyl or phenylalkyl with alkyl as C1–C4, morpholinyl, pyridyl, naphthyl or phenyl optionally substituted with one or more radicals chosen from the radicals C1–C4 alkoxy, halogen, amino, alkylamino and dialkylamino; an aromatic ring as defined above; a quinuclidine radical; a pyrrolidinyl radical which is itself optionally substituted with an alkyl or phenylalkyl radical with alkyl as C1–C4; a piperazinyl radical which is itself optionally substituted with an alkyl, cycloalkyl or phenylalkyl radical; a morpholinyl radical; a pyridyl radical or a piperidyl radical which are optionally substituted with one or more alkyl or phenylalkyl radicals with alkyl C1–C4; an indazolyl radical; a naphthyl radical, a benzotriazole radical; a pyrimidinyl radical optionally substituted with one or more alkyl radicals with alkyl as C1–C4; an acenaphthene radical, it being understood that, when XR1R2 represents NR1R2, then R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a radical chosen from the following radicals: piperazinyl optionally substituted with one or more radicals which are identical or different; pyrrolidinyl optionally substituted with C1–C4 alkyl or alkoxy, hydroxyl, acylamino, pyrrolidinylalkyl and pyridyl; 1,2,3,4-tetrahydroisoquinolinyl; diazepine optionally substituted with alkyl or pyrrolidinylalkyl; piperidyl optionally substituted with alkyl, alkoxy or alkoxyalkyl, hydroxyl and cycloalkylalkyl; morpholinyl; imidazolinyl optionally substituted with alkyl.

The present invention thus relates to the compounds as defined above, characterized in that XR1(R2) is such that, when X represents N, either one of R1 and R2 represents the hydrogen atom or a C1–C4 alkyl radical optionally substituted with an amino, alkylamino, dialkylamino or phenyl radical and the other of R1 and R2 is chosen from the values defined for R1 and R2 in any one of Claims 1 to 8 or R1 and R2 together form with the nitrogen atom to which they are attached a piperazinyl radical optionally substituted with one or more radicals chosen from alkyl, aminoalkyl, alkylaminoalkyl, dialkylaminoalkyl, phenylalkyl, alkoxyalkyl, hydroxyalkyl, hydroxyalkoxyalkyl with alkoxy, pyrrolidinylalkyl, C3–C8 cycloalkyl, pyrazinyl, pyrimidinyl, pyridyl, furylcarbonyl, furfurycarbonyl and quinolyl; pyrrolidinyl optionally substituted with C1–C4 alkyl or alkoxy, hydroxyl, acylamino, pyrrolidinylalkyl and pyridyl; 1,2,3,4-tetrahydroisoquinolinyl; diazepine optionally substituted with alkyl or pyrrolidinylalkyl; piperidyl optionally substituted with alkyl, alkoxy or alkoxyalkyl, hydroxyl and cycloalkylalkyl; morpholinyl; imidazolinyl optionally substituted with alkyl.

The present invention thus relates to the compounds defined above which bind the G-quadruplex structure of the telomeres, characterized in that they correspond to formula (I) below:

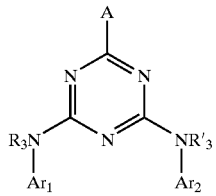

in which:

A represents a radical XR1(R2) in which X represents a nitrogen, oxygen or sulphur atom or a C1–C6 alkyl radical in order to form one of the following radicals:

NR1R2 with R1 and R2, which are identical or different, are chosen from a hydrogen atom; C1–C8 alkyl optionally substituted with a radical amino, alkylamino, dialkylamino, (phenyl)(alkyl)amino, (alkylphenyl)(alkyl)amino, C1–C4 alkoxy, C1–C4 thioalkoxy, trifluoromethyl, pyrrolidinyl, piperidyl, piperazinyl, morpholinyl, pyridyl or phenyl; an aromatic ring as defined in Claim 1; a quinuclidine radical, a radical pyrrolidinyl, piperazinyl, morpholinyl, pyridyl or a piperidyl radical optionally substituted with C1–C4 alkyl it being understood that R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a saturated or unsaturated 3- to 6-membered monocyclic or 8- to 10-membered bicyclic radical optionally containing one or two heteroatoms, which are identical or different, chosen from N, O or S, a group OR1 or SR1 in which R1 has the same meaning as above, it being understood that R1 does not represent hydrogen or unsubstituted C1–C4 alkyl, or an alkyl group containing from 1 to 6 carbon atoms, substituted with R1 R2 as defined above R3 and R'3, which are identical or different, represent independently of one another hydrogen or a C1–C4 alkyl group $Ar_1$ and $Ar_2$, which are identical or different, represent 1. when $Ar_1$ and $Ar_2$ are identical:
   a quinoline motif optionally substituted with at least one group N(Ra)(Rb) in which Ra and Rb, which are identical or different, represent hydrogen or a C1–C4 alkyl radical, (or) a short-chain alkoxy or alkyl group containing 1 to 4 carbon atoms or
   a quinoline possessing a nitrogen atom in quaternary form or
   a benzamidine or
   a pyridine attached at the 4-position or fused with an aryl or heteroaryl group optionally substituted with a C1–C4 alkyl group 2. when $Ar_1$ and $Ar_2$ are different
   $Ar_1$ and $Ar_2$ both represent one of the possibilities mentioned above for $Ar_1$ and $Ar_2$ or
   $Ar_1$ represents one of the above possibilities and $Ar_2$ represents
      a phenyl ring optionally substituted with a halogen group, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group for each alkyl group, nitro group, C1–C4 alkyleneamino group, (or) C2–C4 alkenyleneamino group, or a piperazinyl radical optionally substituted with a C1–C4 alkyl radical,
      a mono- or bi- or tricyclic heterocyclic ring comprising 0 to 2 heteroatoms per ring provided that at least one heteroatom is present in at least one ring optionally substituted with one or more C1–C4 alkyl groups or with C1–C4 alkylene or C2–C4 alkenylene groups or one of its salts, these compounds of formula (I) being in all the possible isomeric forms, racemates, enantiomers and diastereoisomers.

The present invention also relates to the novel compounds characterized in that they correspond to formula (I) below:

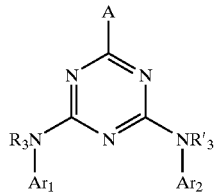

in which:

A represents a radical XR1(R2) in which X represents a nitrogen, oxygen or sulphur atom or a C1–C6 alkyl radical in order to form one of the following radicals:

NR1R2 with R1 and R2, which are identical or different, are chosen from a hydrogen atom; C1–C8 alkyl optionally substituted with a radical amino, alkylamino, dialkylamino, (phenyl)(alkyl)amino, (alkylphenyl)(alkyl)amino, C1–C4 alkoxy, C1–C4 thioalkoxy, trifluoromethyl, pyrrolidinyl, piperidyl, piperazinyl, morpholinyl, pyridyl or phenyl; an aromatic ring as defined in Claim 1; a quinuclidine radical, a radical pyrrolidinyl, piperazinyl, morpholinyl, pyridyl or a piperidyl radical optionally substituted with C1–C4 alkyl it being understood that R1 and R2, which are identical, both do not represent hydrogen or unsubstituted C1–C4 alkyl and R1 and R2, which are different, do not represent one hydrogen and the other unsubstituted C1–C4 alkyl or alternatively, when X represents N or alkyl, R1 and R2 together form with X to which they are attached a saturated or unsaturated 3- to 6-membered monocyclic or 8- to 10-membered bicyclic radical optionally containing one or two heteroatoms, which are identical or different, chosen from N, O or S, a group OR1 or SR1 in which R1 has the same meaning as above, it being understood that R1 does not represent hydrogen or unsubstituted C1–C4 alkyl, or an alkyl group containing from 1 to 6 carbon atoms, substituted with R1 R2 as defined above R3 and R'3, which are identical or different, represent independently of one another hydrogen or a C1–C4 alkyl group $Ar_1$ and $Ar_2$, which are identical or different, represent
when $Ar_1$ and $Ar_2$ are identical:
a quinoline motif optionally substituted with at least one group N(Ra)(Rb) in which Ra and Rb, which are identical or different, represent hydrogen or a C1–C4 alkyl radical, (or) a short-chain alkoxy or alkyl group containing 1 to 4 carbon atoms or
a quinoline possessing a nitrogen atom in quaternary form or
a benzamidine or
a pyridine attached at the 4-position or fused with an aryl or heteroaryl group optionally substituted with a C1–C4 alkyl group when $Ar_1$ and $Ar_2$ are different
$Ar_1$ and $Ar_2$ both represent one of the possibilities mentioned above for $Ar_1$ and $Ar_2$ or
$Ar_1$ represents one of the above possibilities and $Ar_2$ represents
a phenyl ring optionally substituted with a halogen group, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group for each alkyl group, nitro group, C1–C4 alkyleneamino group, (or) C2–C4 alkenyleneamino group, or a piperazinyl radical optionally substituted with a C1–C4 alkyl radical,
a mono- or bi- or tricyclic heterocyclic ring comprising 0 to 2 heteroatoms per ring provided that at least one heteroatom is present in at least one ring optionally substituted with one or more C1–C4 alkyl groups or with C1–C4 alkylene or C2–C4 alkenylene groups or one of its salts, these compounds of formula (I) being in all the possible isomeric forms, racemates, enantiomers and diastereoisomers.

The present invention relates in particular to the compounds of formula (I) as defined above in which A represents a radical XR1(R2) in which X represents a nitrogen atom N in order to form NR1R2, an oxygen atom O in order to form OR1 or a sulphur atom S in order to form SR1 as follows:
NR1R2 with R1 and R2, which are identical or different, are chosen from a hydrogen atom; C1–C8 alkyl optionally substituted with a radical amino, alkylamino, dialkylamino, (phenyl)(alkyl)amino, (alkylphenyl)(alkyl)amino, C1–C4 alkoxy, with a radical pyrrolidinyl, pyridyl or with a phenyl radical; an aromatic ring as defined in Claim 1; a quinuclidine radical, a pyrrolidinyl radical or a piperidyl radical optionally substituted with C1–C4 alkyl it being understood that R1 and R2, which are identical, both do not represent hydrogen or unsubstituted C1–C4 alkyl and R1 and R2, which are different, do not represent one hydrogen and the other unsubstituted C1–C4 alkyl,
or alternatively, when X represents N, R1 and R2 together form with X to which they are attached a piperazinyl, piperidyl, pyrrolidinyl, morpholinyl or thiomorpholinyl radical,
or a group OR1 or SR1 in which R1 has the same meaning as above it being understood that R1 does not represent hydrogen or unsubstituted C1–C4 alkyl.

The present invention relates more specifically to the compounds of formula (I) as defined above in which, when A represents NR1R2, either one of R1 and R2 represents a hydrogen atom and the other of R1 and R2 is chosen from the values defined for R1 and R2, or R1 and R2 together form with the nitrogen atom to which they are attached a piperazinyl, pyrrolidinyl, piperidyl or morpholinyl radical.

The present invention also relates more specifically to the compounds of formula (I) as defined above in which the group A represents:
either an amino radical substituted with a radical chosen from the following groups: 4-amino- or 4-methylamino- or 4-dimethylaminoquinolyl or -quinolinium in which the quinolinium ring is optionally substituted with a group methyl; pyridyl; phenyl optionally substituted with one or more halogen atoms or with a radical piperazinyl or alkylpiperazinyl; C1–C4 alkyl substituted with a radical amino, alkylamino or dialkylamino, (phenyl)(alkyl)amino, (alkylphenyl)(alkyl)amino, C2–C4 alkoxy, with a pyrrolidinyl radical or with a phenyl radical, in which radicals the alkyl groups possess 1 to 4 carbon atoms; a pyrrolidinyl radical; a piperidyl radical optionally substituted with a C1–C4 alkyl radical; or a quinuclidine radical
or a pyrrolidinyl radical, a morpholino radical or a piperazinyl radical optionally substituted with a C1–C4 alkyl radical
or a radical O-phenyl, O-pyridyl or O-alkyl substituted with an amino, alkylamino or dialkylamino radical Among the compounds defined above, there are mentioned particularly the compounds characterized in that $Ar_1$ and $Ar_2$ represent a group chosen from the following groups: 4-amino- or 4-methylamino- or 4-dimethylaminoquinolyl or -quinolinium in which the quinolinium ring is optionally substituted with a group methyl; or phenyl optionally substituted with one or more halogen atoms.

Among the compounds defined above, there are also mentioned particularly the compounds characterized in that the group A represents:
either an amino radical substituted with a radical chosen from the following groups: 4-amino- or 4-methylamino- or 4-dimethylaminoquinolyl or -quinolinium in which the quinolinium ring is optionally substituted with a group methyl; pyridyl; phenyl optionally substituted with one or more halogen atoms or with a radical piperazinyl or alkylpiperazinyl; C1–C4 alkyl substituted with a radical amino, alkylamino or dialkylamino, (phenyl)(alkyl)amino, (alkylphenyl)(alkyl)amino, C2–C4 alkoxy, with a pyrrolidinyl radical or with a phenyl radical, in which radicals the alkyl groups possess 1 to 4 carbon atoms; a pyrrolidinyl radical; a piperidyl radical optionally substituted with a C1–C4 alkyl radical; or a quinuclidine radical
or a pyrrolidinyl radical, a morpholino radical or a piperazinyl radical optionally substituted with a C1–C4 alkyl radical
or a radical O-phenyl, O-pyridyl or O-alkyl substituted with an amino, alkylamino or dialkylamino radical.

Among the compounds defined above, there are further particularly mentioned the compounds characterized in that, when $Ar_1$ and $Ar_2$ are identical, $Ar_1$ and $Ar_2$ represent a group chosen from the groups 4-amino- or 4-methylamino- or 4-dimethylaminoquinolyl or -quinolinium in which the quinolinium ring is optionally substituted with a methyl group.

Among the compounds defined above, there are mentioned particularly the compounds characterized in that, when $Ar_1$ and $Ar_2$ are different,
1. $Ar_1$ represents:
a quinoline motif substituted with at least one group N(Ra)(Rb) in which Ra and Rb, which are identical or different, represent hydrogen or a C1–C4 alkyl radical or a short-chain alkoxy or alkyl group containing 1 to 4 carbon atoms, or a quinoline possessing a nitrogen atom in quaternary form or a benzamidine except in the case where A represents diethylamine, hydrogen or an amine group or a pyridine attached at the 4-position or fused with an aryl or heteroaryl group 2. Ar$_2$ represents a ring as defined above but different or a phenyl ring optionally substituted with a halogen, methoxy, cyano, carbonylamino, guanyl, methylthio, amino, methylamino, dimethylamino, morpholine, C1–C4 alkyleneamino or C2–C4 alkenyleneamino group a quinoline, benzimidazole, indole, benzothiophene, benzofuran, benzothiazole, benzoxazole, carbazole, quinazoline or quinoxaline ring optionally substituted with one or more C1–C4 alkyl groups or with C1–C4 alkylene or C2–C4 alkenylene groups Among the compounds defined above, there are mentioned more particularly the compounds characterized in that A represents an amino radical substituted with a radical chosen from the following groups: 4-amino- or 4-methylamino- or 4-dimethylaminoquinolinyl or -quinolinium radicals in which the quinolinium ring is optionally substituted with a methyl group; C1–C4 alkyl radicals substituted with an amino, alkylamino, dialkylamino, (phenyl)(alkyl)amino, (alkylphenyl)(alkyl)amino, pyrrolidinyl or pyridyl radical; or the quinuclidine radical.

Among the compounds defined above, there are also mentioned the compounds characterized in that A represents either an amino radical substituted with a radical pyridyl; phenyl optionally substituted with a piperazinyl or alkylpiperazinyl radical; a piperidyl radical optionally substituted with a C1–C4 alkyl radical or a piperazinyl radical optionally substituted with a C1–C4 alkyl radical.

There are mentioned in particular the compounds as defined above, characterized in that A represents a radical O(or S)-aromatic ring or a radical O(or S)-alkyl with alkyl optionally substituted.

Among the compounds defined above, there are further mentioned the compounds characterized in that A represents a radical O-phenyl, O-pyridyl, or O-alkyl substituted with an amino, alkylamino or dialkylamino radical.

It is evident that the quinoline motifs may be substituted by any other group not involved in the intended application; thus, acridine or isoquinoline or quinazoline or quinoxaline or phthalazine or benzothiazine or benzoxazine or phenoxazine or phenothiazine groups are included in the definition of the quinoline groups.

Among the above compounds of formula (I), there are preferred those comprising two heterocycles chosen from the 4-aminoquinolyl, 4-aminoquinolinium or quinolinium groups in which the quinolinium ring is optionally substituted with a methyl group.

Among the preferred products as defined above, there may be mentioned the products of Examples 1, 2, 11, 17, 19, 20, 27, 29, 31, 32 and 33 of Table 1 below which therefore correspond respectively to the compounds whose names follow:

2,4-bis(4-dimethylamino-2-methylquinolin-6-yl)amino-6-(3-dimethylaminopropyl)amino-[1,3,5]triazine (Example 1)

2,4,6-tris(4-amino-2-methylquinolin-6-yl)amino-[1,3,5]triazine (Example 2)

2,4-bis(4-amino-2-methylquinolin-6-yl)amino-6-(4-dimethylamino-2-methylquinolin-6-yl)amino-[1,3,5]triazine (Example 11)

2,4-bis(4-amino-2-methylquinolin-6-yl)amino-6-(quinuclidin-3-yl)amino-[1,3,5]triazine (Example 17)

2,4-bis(4-dimethylamino-2-methylquinolin-6-yl)amino-6-(1-methylpiperidin-4-yl)-[1,3,5]triazine (Example 19)

2,4-bis(4-dimethylamino-2-methylquinolin-6-yl)amino-6-(1-methylpiperazin-4-yl)-[1,3,5]triazine (Example 20)

2,4-bis(4-dimethylamino-2-methylquinolin-6-yl)amino-6-(pyridin-4-yl)methylamino-[1,3,5]triazine (Example 27)

2,4-bis(4-amino-2-methylquinolin-6-yl)amino-6-phenoxy-[1,3,5]triazine (Example 29)

2,4-bis(4-amino-2-methylquinolin-6-yl)amino-6-(3-dimethylaminopropyl)oxy-[1,3,5]triazine (Example 31)

2,4-bis(4-amino-2-methylquinolin-6-yl)amino-6-(pyridin-4-yl)oxy-[1,3,5]triazine (Example 32)

2,4-bis(4-amino-2-methylquinolin-6-yl)amino-6-(phenylmethyl)oxy-[1,3,5]triazine (Example 33).

Among the preferred products of the present invention as defined above, there may be mentioned particularly the products of Table 1 below which correspond to the compounds whose names follow:

2,4-bis(4-dimethylamino-2-methylquinolin-6-yl)amino-6-(3-dimethylaminopropyl)amino-[1,3,5]triazine (Example 1)

2,4,6-tris(4-amino-2-methylquinolin-6-yl)amino-[1,3,5]triazine (Example 2)

2,4-bis(4-amino-2-methylquinolin-6-yl)amino-6-(4-dimethylamino-2-methylquinolin-6-yl)amino-[1,3,5]triazine (Example 11)

2,4-bis(4-dimethylamino-2-methylquinolin-6-yl)amino-6-(1-methylpiperazin-4-yl)-[1,3,5]triazine (Example 20)

2,4-bis(4-dimethylamino-2-methylquinolin-6-yl)amino-6-(pyridin-4-yl)oxy-[1,3,5]triazine (Example 115)

2,4-bis(4-amino-2-methylquinolin-6-yl)amino-6-(quinolin-2-yl)thio-[1,3,5]triazine (Example 128)

2,4-bis(4-dimethylamino-2-methylquinolin-6-yl)amino-6-phenyl-[1,3,5]triazine (Example 134)

2,4-bis(4-dimethylamino-2-methylquinolin-6-yl)amino-6-[1-(2-dipropylaminoethyl)piperazin-4-yl]-[1,3,5]triazine (Example 137)

2,4-bis(4-dimethylamino-2-methylquinolin-6-yl)amino-6-{[1-2-(2-hydroxyethyl)oxyethyl]piperazin-4-yl}-[1,3,5]triazine (Example 141)

2,4-bis(4-dimethylamino-2-methylquinolin-6-yl)amino-6-[2(S)-(pyrrolidin-1-yl)methylpyrrolidin-1-yl]-[1,3,5]triazine (Example 149)

2,4-bis(4-dimethylamino-2-methylquinolin-6-yl)amino-6-(quinolin-2-yl)thio-[1,3,5]triazine (Example 133)

2,4-bis(4-dimethylamino-2-methylquinolin-6-yl)amino-6-(1-methylhomopiperazin-4-yl)-[1,3,5]triazine (Example 135)

2,4-bis(4-dimethylamino-2-methylquinolin-6-yl)amino-6-[1-(3-dimethylaminopropyl)piperazin-4-yl]-[1,3,5]triazine (Example 136)

2,4-bis(4-dimethylamino-2-methylquinolin-6-yl)amino-6-[N-(1-methylpiperidin-4-yl)-N-methylamino]-[1,3,5]triazine (Example 138)

2,4-bis(4-dimethylamino-2-methylquinolin-6-yl)amino-6-{1-[3-(pyrrolidin-1-yl)propylhomopiperazin-4-yl)-[1,3,5]triazine (Example 139)

2,4-bis(4-dimethylamino-2-methylquinolin-6-yl)amino-6-[1-(pyridin-4-yl)piperazin-4-yl]-[1,3,5]triazine (Example 144)

Among the preferred products of the present invention as defined above, there may be mentioned most particularly the products of Table 1 below which correspond to the compounds whose names follow:

2,4-bis(4-dimethylamino-2-methylquinolin-6-yl)amino-6-(1-methylpiperazin-4-yl)-[1,3,5]triazine (Example 20)

2,4-bis(4-dimethylamino-2-methylquinolin-6-yl)amino-6-(quinolin-2-yl)thio-[1,3,5]triazine (Example 133)

2,4-bis(4-dimethylamino-2-methylquinolin-6-yl)amino-6-(1-methylhomopiperazin-4-yl)-[1,3,5]triazine (Example 135)

2,4-bis(4-dimethylamino-2-methylquinolin-6-yl)amino-6-[1-(3-dimethylaminopropyl)piperazin-4-yl]-[1,3,5]triazine (Example 136)

2,4-bis(4-dimethylamino-2-methylquinolin-6-yl)amino-6-[N-(1-methylpiperidin-4-yl)-N-methylamino]-[1,3,5]triazine (Example 138)

2,4-bis(4-dimethylamino-2-methylquinolin-6-yl)amino-6-{1-[3-(pyrrolidin-1-yl)propylhomopiperazin-4-yl)-[1,3,5]triazine (Example 139)

2,4-bis(4-dimethylamino-2-methylquinolin-6-yl)amino-6-[1-(pyridin-4-yl)piperazin-4-yl]-[1,3,5]triazine (Example 144).

Another subject of the present invention relates to the use of the compounds of the formula (I) as pharmaceutical product for human use.

The subject of the present invention is most particularly the pharmaceutical compositions comprising, as active ingredient, a product of formula (I) as defined above.

The subject of the present invention is most particularly the pharmaceutical compositions comprising, as active ingredient, a product of formula (I) of Table 1 below.

The subject of the present invention is most particularly the pharmaceutical compositions comprising, as active ingredient, a product of formula (I) chosen from those whose names are mentioned above.

The invention therefore extends to the pharmaceutical compositions containing, as active ingredient, at least one of the medicaments as defined above.

These pharmaceutical compositions may be administered orally, parenterally or locally as a topical application to the skin and the mucous membranes or by injection intravenously or intramuscularly.

These compositions may be solids or liquids and may be provided in any pharmaceutical form commonly used in human medicine such as, for example, simple or sugar-coated tablets, pills, lozenges, gelatin capsules, drops, granules, injectable preparations, ointments, creams or gels; they are prepared according to the customary methods. The active ingredient may be incorporated therein with excipients normally used in these pharmaceutical compositions, such as talc, gum arabic, lactose, starch, magnesium stearate, cocoa butter, aqueous or nonaqueous vehicles, fatty substances of animal or plant origin, paraffin derivatives, glycols, various wetting, dispersing or emulsifying agents, preservatives.

The processes for preparing the compounds of formula (I):

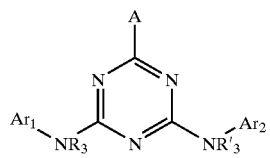

are described below.

General Method 1

According to a first preparation method, compounds of general formula (I) in which $Ar_1$ and $Ar_2$ on the one hand and $R_3$ and $R'_3$ on the other hand are identical and defined as above and R represents a halogen atom such as chlorine or fluorine, an amino, alkylamino or dialkylamino function in which the straight or branched alkyl portions contain from 1 to 4 carbon atoms, an alkyloxy or alkylthio function in which the straight or branched alkyl portions contain from 1 to 4 carbon atoms, an alkyloxy or alkylthio function in which the straight or branched alkyl portions contain from 1 to 4 carbon atoms, may be obtained by amination of a dihalotriazine, most generally a dichloro-s-triazine, of general formula (B) in which A is as defined above, with an aromatic or heteroaromatic amine of general formula (C) in which Ar is as defined above, the procedure being carried out according to scheme 1:

Scheme 1

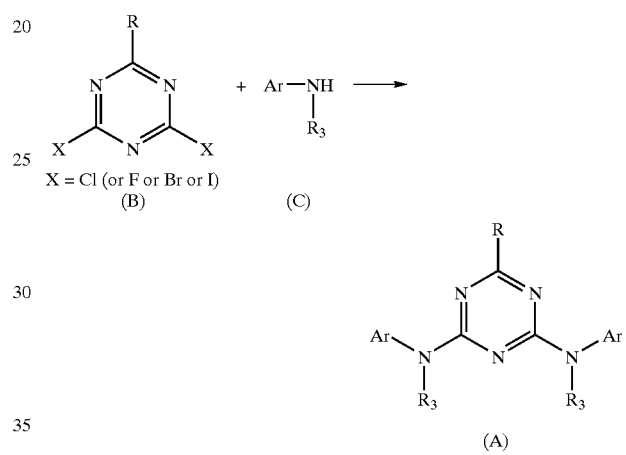

In the case where A represents a halogen atom, it is useful to react the corresponding 2,4,6-trihalo-s-triazine of general formula (B) with the aromatic or heteroaromatic amine $ArNHR_3$ of general formula (C).

The procedure is generally carried out by condensing one mole of dihalo-s-triazine, or trihalo-s-triazine, with 2 moles of aromatic or heteroaromatic amine. The reaction takes place in an inert medium under the reaction conditions. There may be mentioned, among the inert solvents, acetone which is optionally aqueous or an alcohol which is optionally aqueous such as ethanol, or a halogenated solvent such as dichloromethane, or an ether such as diethyl ether or dioxane, or a polar aprotic solvent such as DMF, DMSO or NMP. The procedure is preferably carried out at a temperature of between 20° C. and the reflux temperature, in the presence in particular of an organic base such as triethylamine, or an inorganic base such as sodium hydroxide or sodium or potassium carbonate. It is also possible not to use a base during the amination reaction, and to isolate a hydrochloride of the product of general formula (A), whose base can then be released.

The dihalo- or trihalo-s-triazines of general formula (B) are either commercially available or are known, and may be obtained under the conditions described in the literature.

The aromatic or heteroaromatic amines of general formula (C) are either known or may be easily prepared by the known methods of synthesizing aromatic or heteroaromatic amines.

In the case where $Ar_1$ and $Ar_2$ are different, the triazine of general formula (A) may be obtained by sequential displacement of the halogen atoms, most generally of the chlorine atoms, from the products of general formula (B) by the amines $Ar_1NHR_3$ and then $Ar_2NHR'_3$ of general formula (C) according to scheme 2:

Scheme 2

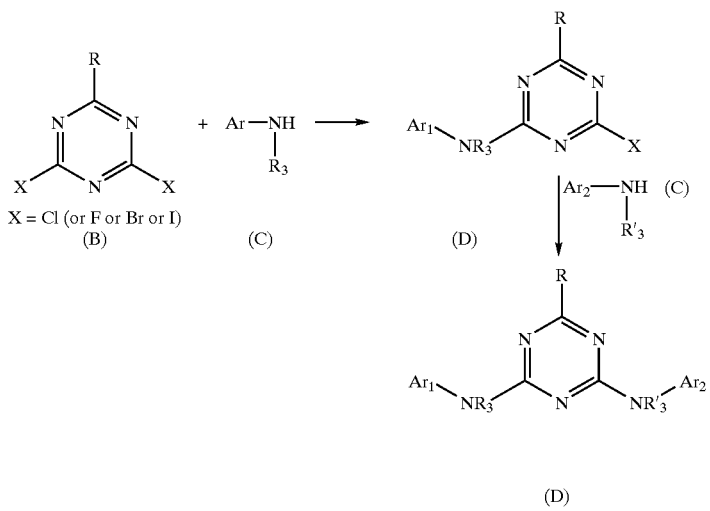

Generally, the procedure is carried out with 1 mole of dihalo-s-triazine, or trihalo-s-triazine, and 1 mole of amine $Ar_1NHR_3$. The procedure is preferably carried out in an inert solvent such as acetone which is optionally aqueous or an alcohol which is optionally aqueous, such as ethanol, or a halogenated solvent such as dichloromethane, or an ether such as diethyl ether or dioxane, or a polar aprotic solvent such as DMF, DMSO or NMP. According to a better way of carrying out the invention, the procedure is carried out at a temperature of between 20° C. and 50° C. Next, 1 mole of amine $Ar_2NHR'_3$ is added to the product of general formula (D), which may be optionally isolated. The procedure is carried out in particular at a temperature of between 50° C. and the reflux temperature.

Advantageously, it is possible to carry out the procedure under the conditions described in J. Fluor. Chem., 1988, 39(1), 117–123.

General Method 2

According to a second method, the products of general formula (A) in which $Ar_1NHR_3$ and $Ar_2NHR'_3$ are as defined above and R represents a group NR1R2 or OR1 or SR1 or alkR1R2 may also be prepared by nucleophilic displacement of a halogen atom, generally a chlorine atom, from a product of general formula (A) in which R represents a halogen atom according to scheme 3:

Scheme 3

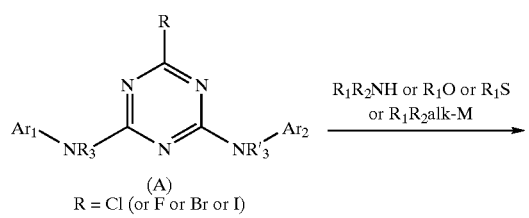

-continued

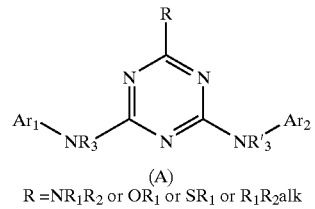

(A)
R =$NR_1R_2$ or $OR_1$ or $SR_1$ or $R_1R_2alk$

The procedure is generally carried out by condensing 1 mole of product of general formula (A) in which R represents a halogen atom, preferably a chlorine atom, with 1 mole of amine R1R2NH or alcoholate R1O⁻ or thioalcoholate R1S or organometallic R1R2alkM, it being possible for M to represent, for example, magnesium or lithium or zinc. The reaction takes place in an inert medium under the reaction conditions. There may be mentioned among the inert solvents acetone which is optionally aqueous or an alcohol which is optionally aqueous such as ethanol, or a halogenated solvent such as dichloromethane, or an ether such as diethyl ether or dioxane or tetrahydrofuran, it being understood that these ethers are solvents which can be used when an organometallic R1R2alkM is used, or a polar aprotic solvent such as DMF, DMSO or NMP. When the entering group represents a group R1R2NH, the procedure is preferably carried out at a temperature of between 20° C. and the reflux temperature, in the presence in particular of an organic base such as triethylamine, or an inorganic base such as sodium hydroxide or sodium or potassium carbonate. It is also possible not to use a base during the amination reaction, and to isolate a hydrochloride of the product of general formula (A), the base of which can then be released. When the entering group represents a group R1O⁻ or R1S⁻, the procedure is preferably carried out with an alkali metal or alkaline-earth metal alcoholate or thioalcoholate, such as a sodium or potassium or lithium or ammonium or caesium or barium salt, in a polar aprotic solvent such as DMF or DMSO or NMP, at a temperature of between 50° C. and the reflux temperature. When the entering group represents a group R1R2alk, the procedure is most preferably carried out in an ether such as diethyl ether or dioxane or tetrahydrofuran, at a temperature of between −70° C. and the reflux temperature of the reaction medium.

It is understood that the s-triazines of general formula may be obtained in the form of libraries, by applying the methods described in schemes 1, 2 or 3 in parallel and/or combinatorial chemistry in liquid phase or in solid phase, it being understood that, when the work is carried out in solid phase, any of the reagents is attached beforehand onto a solid support, chosen according to the chemical reaction involved, and that said chemical reaction is followed by an operation of cleaving the product of the reaction from the solid support.

The present invention also relates to therapeutic compositions containing a compound according to the invention, in combination with a pharmaceutically acceptable carrier according to the mode of administration chosen. The pharmaceutical composition may be provided in solid, liquid or liposome form.

Among the solid compositions, there may be mentioned powders, gelatin capsules and tablets. Among the oral forms, it is also possible to include the solid forms which are protected from the acidic medium of the stomach. The carriers used for the solid forms consist in particular of inorganic carriers such as phosphates, carbonates or organic carriers such as lactose, celluloses, starch or polymers. The liquid forms consist of solutions, suspensions or dispersions. They contain, as dispersive carrier, either water or an organic solvent (ethanol, NMP and the like) or mixtures of surfactants and solvents or of complexing agents and solvents.

The administered dose of the compounds of the invention will be adjusted by the practitioner according to the route of administration, the patient and the condition of the latter.

The compounds of the present invention may be administered alone or mixed with other anticancer agents. Among the possible combinations, there may be mentioned alkylating agents and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as in particular cisplatin, carboplatin or oxaliplatin antibiotic agents such as in particular bleomycin, mitomycin, dactinomycin, antimicrotubule agents such as in particular vinblastine, vincristine, vindesine, vinorelbine, taxoids (paclitaxel and docetaxel)

anthracyclines such as in particular doxorubicin, daunorubicin, idarubicin, epirubicin, mitoxantrone, losoxantrone group I and II topoisomerases such as etoposide, teniposide, amsacrine, irinotecan, topotecan and tomudex, fluoropyrimidines such as 5-fluorouracil, UFT, floxuridine, cytidine analogues such as 5-azacytidine, cytarabine, gemcitabine, 6-mercaptomurine, 6-thioguanine adenosine analogues such as pentostatin, cytarabine or fludarabine phosphate methotrexate and folinic acid various enzymes and compounds such as L-asparaginase, hydroxyurea, trans-retinoic acid, suramine, dexrazoxane, amifostine, herceptin as well as oestrogenic and androgenic hormones antivascular agents such as combretastatin and colchicine derivatives and their prodrug.

It is also possible to combine a radiation treatment with the compounds of the present invention. These treatments may be administered simultaneously, separately or sequentially. The treatment will be adapted to the patient to be treated by the practitioner.

The G-quadruplex stabilizing activity may be determined by a method using the formation of a complex with fluorescein of which the experimental protocol is described below.

Oligonucleotides

All the nucleotides, modified or otherwise, were synthesized by Eurogentec SA, Seraing, Belgium. The oligonucleotide FAM+DABCYL carries the catalogue reference OL-0371-0802. It has the sequence: GGGTTAGGGT-TAGGGTTAGGG corresponding to 3.5 repeats of the human telomereic motif (strand rich in G). The fluorescein is attached to the 5' end, the DABCYL to the 3' end, by the chemical arms described by Eurogentec. The concentration of the samples is checked by spectrophotometry, recording the absorbance spectrum between 220 and 700 nm and using the molar extinction coefficient provided by the supplier.

Buffers

All the experiments were carried out in a 10 mM sodium cacodylate buffer pH 7.6 containing 0.1 M lithium chloride (or sodium chloride). The absence of fluorescent contamination in the buffer was checked beforehand. The fluorescent oligonucleotide is added at the final concentration of 0.2 $\mu$M.

Study of Fluorescence

All the measurements of fluorescence were carried out on a Spex Fluorolog DM1B apparatus, using an excitation line width of 1.8 nm and an emission line width of 4.5 nm. The samples are placed in a microquartz cuvette of 0.2×1 cm. The temperature of the sample is controlled by an external water bath. The oligonucleotide alone was analysed at 20, 30, 40, 50, 60, 70 and 80° C. The emission spectra are recorded using an excitation wavelength of 470 nm. The excitation spectra are recorded using either 515 nm or 588 nm as emission wavelength. The spectra are corrected for the response of the instrument by reference curves. A high extinction (80–90%) of the fluorescence of fluorescein at room temperature is observed, in agreement with an intramolecular folding of the oligonucleotide at 20° C. in the form of a G-quadruplex, which induces juxtaposition of its 5' and 3' ends which are respectively linked to fluorescein and to DABCYL. This juxtaposition causes an already-described phenomenon of extinction of fluorescence which is used for "molecular beacons".

Fluorescence Tm

An oligonucleotide stock solution at the strand concentration of 0.2 $\mu$M in 0.1 M LiCl, 10 mM cacodylate buffer, pH 7.6, is prepared beforehand, heated briefly at 90° C. and slowly cooled to 20° C., and then distributed in aliquots of 600 $\mu$l in the fluorescence cuvettes. 3 $\mu$l of water (for the control) or 3 $\mu$l of test product (stock at 200 $\mu$M, final concentration 1 $\mu$M) are then added and mixed. The samples are then allowed to incubate for at least 1 hour at 20° C. before each measurement. The use of longer incubation times (up to 24 hours) has no influence on the result obtained.

Each experiment allows the measurement of only one sample. The latter is first incubated at an initial temperature of 20° C., heated to 80° C. over 38 minutes, left for 5 minutes at 80° C. and then cooled to 20° C. over 62 minutes.

During this time, the fluorescence is measured simultaneously at two emission wavelengths (515 nm and 588 nm) using 470 nm as excitation wavelength. A measurement is carried out every 30 seconds. The temperature of the water bath is recorded in parallel, and the fluorescence profile as a function of the temperature is reconstituted from these values. The fluorescence profiles are then normalized between 20° C. and 80° C., and the temperature for which the intensity of emission at 515 nm is the mean of those at high and low temperature is called Tm. Under these conditions, the Tm of the reference sample without addition of product is 44° C. in a lithium chloride buffer. This temperature is increased to more than 55° C. in a sodium chloride buffer. The addition of a G-quadruplex-stabilizing compound induces an increase in the Tm. This increase is judged to be significant if it is greater than 3°.

The antitelomerease biological activity is determined by the following experimental protocol:

Preparation of the Extract Enriched in Human Telomerease Activity

The leukaemia line HL60 is obtained from ATCC (American Type Culture Collection, Rockville, USA). The cells are cultured in suspension in RPMI 1640 medium containing L-glutamine at 2 mM, penicillin 200 U/ml, streptomycin 200 µg/ml, gentamycin 50 µg/ml and supplemented with 10% heat-inactivated foetal calf serum.

An aliquot of $10^5$ cells is centrifuged at 3000×G and the supernatant discarded. The cell pellet is resuspended by several successive pipettings in 200 µl of lysis buffer containing 0.5% CHAPS, 10 mM Tris-HCl, pH 7.5, 1 mM $MgCl_2$, 1 mM EGTA, 5 mM β-mercaptoethanol, 0.1 mM PMSF and 10% glycerol and is stored in ice for 30 minutes. The lysate is centrifuged at 160,000×G for 20 minutes at 4° C. and 160 µl of supernatant are recovered. The proteins in the extract are assayed by the Bradford method. The extract is stored at −80° C.

Assay of the Telomerease Activity

The inhibition of the telomerease activity is determined by a protocol for extension of the oligonucleotide TS (5'AATCGTTCGAGCAGAGTT3'), in the presence of a cellular extract enriched in telomerease activity and compounds which are added at various concentrations (10, 1, 0.1 and 0.01 µM). The extension reaction is followed by a PCR amplification of the extension products with the aid of the oligonucleotides TS and CXext (5'GTGCCCTTACCCTTACCCTTACCCTAA3').

The reaction medium is prepared based on the following composition:

| Tris HCl pH 8.3 | 20 mM |
|---|---|
| MgC12 | 1.5 mM |
| Tween 20 | 0.005% (Ply) |
| EGTA | 1 mM |
| dATP | 50 µM |
| dGTP | 50 µM |
| dCTP | 50 µM |
| dTTP | 50 µM |
| Oligonucleotide TS | 2 µg/ml |
| Oligonucleotide CXext | 2 µg/ml |
| Bovine serum albumin | 0.1 mg/ml |
| Taq DNA polymerase | 1 U/ml |
| alpha 32P dCTP (3000 Ci/mmol) | 0.5 µl |
| Telomerease extract | 200 ng in a volume of 10 µl |
| Test product or solvent | in a volume of 5 µl |
| Double-distilled water QS | 50 µl |

The oligonucleotides are obtained from Eurogentec (Belgium) and are stored at −20° C. at a stock concentration of 1 mg/ml in distilled water.

The reaction samples are assembled in 0.2 ml PCR tubes and one drop of paraffin oil is deposited on each of the reactions of the experiment before closing the tubes.

The reaction samples are then incubated in a Cetus 4800-type PCR apparatus under the following temperature conditions:

15 minutes at 30° C., 1 minute at 90° C., followed by 30 cycles of, 30 seconds at 94° C., 30 seconds at 50° C., and 1 minute 30 seconds at 72° C., followed by a final cycle of 2 minutes at 72° C.

For each of the samples, an aliquot of 10 µl is pipetted under the oil layer and mixed with 5 µl of a loading buffer containing:

| TBE | 3X |
|---|---|
| glycerol | 32% (P/V) |
| bromophenol blue | 0.03% |
| xylene cyanol | 0.03% |

The samples are then analysed by electrophoresis on 12% acrylamide gel in a 1×TBE buffer for 1 hour at a voltage of 200 volts, with the aid of a Novex electrophoresis system.

The acrylamide gels are then dried on a sheet of Whatmann 3 mm paper at 80° C. for 1 hour.

The analysis and the quantification of the reaction products are carried out with the aid of an InstantImager apparatus (Pacard).

For each compound concentration tested, the results are expressed as percentage inhibition of the reaction and calculated from the untreated enzymatic control and from the enzyme-free sample (blank) according to the following formula:

(compound value−blank value/enzymatic control value−blank value)×100.

The concentration of compound inducing a 50% inhibition of the telomerease reaction (IC50) is determined with the aid of a semilogarithmic graphical representation of the inhibition values obtained as a function of each of the compound concentrations tested.

A compound is considered to be active as an antitelomerease agent when the quantity inhibiting 50% of the telomerease reaction is in particular less than 5 µM.

The cytotoxic biological activity on human tumour lines is determined according to the following experimental protocol:

The human cell lines A549 are obtained from ATCC (American Type Culture Collection, Rockville, USA). The A549 cells are cultured in a layer in a culture flask in RPMI 1640 medium containing L-glutamine at 2 mM, penicillin 200 U/ml, streptomycin 200 µg/ml and supplemented with 10% heat-inactivated foetal calf serum. The KB cells are cultured in a layer in a culture flask in Dulbelco's medium containing L-glutamine at 2 mM, penicillin 200 U/ml, streptomycin 200 µg/ml and supplemented with 10% heat-inactivated foetal calf serum.

The cells at the exponential growth phase are trypsinized, washed in 1×PBS and are inoculated in 96-well microplates (Costar) in an amount of 4×10⁴ cells/ml for A549 and of 1.5×10⁴ cells/ml (0.2 ml/well) and then incubated for 96 hours in the presence of variable concentrations of product to be studied (10, 1, 0.1 and 0.01 $\mu$M, each point in quadruplicate). 16 hours before the end of the incubation, 0.02% final of neutral red is added to each well. At the end of the incubation, the cells are washed with 1×PBS and lysed with 1% sodium lauryl sulphate. The cellular incorporation of the dye, which reflects cellular growth, is evaluated by spectro-photometry at a wavelength of 540 nm for each sample with the aid of a Dynatech MR5000 reading apparatus.

For each compound concentration tested, the results are expressed as percentage of inhibition of cellular growth and calculated from the untreated control and the culture medium free of cells (blank) according to the following formula:

(compound value−blank value/cell control value−blank value)× 100.

The concentration of compound inducing a 50% inhibition of growth (IC50) is determined with the aid of a semilogarithmic graphical representation of the inhibition values obtained as a function of each of the compound concentrations tested.

A compound is considered to be active as cytotoxic agent if the concentration inhibiting the growth of the tumour cells tested by 50% is in particular less than 10 $\mu$M.

The following non-limiting examples are given to illustrate the invention.

Table 1 below gives the chemical structures as well as the G-quartet, antitelomerease and cytotoxic activities of 176 products which constitute, in the chronological order in which they appear in this table, Examples 1 to 176 of the present invention which illustrate the present invention without, however, limiting it. In Table 1 below, 'no' appears when the product does not possess a substituent in the corresponding column in agreement with the chemical definition of the products of the present invention.

EXAMPLE 1

Preparation of 2,4-bis(4-dimethylamino-2-methylquinolin-6-yl)amino-6-(3-dimethylaminopropyl)amino-[1,3,5]triazine 0.5 g (0.0036 mol) of potassium carbonate, 1 g (0.00189 mol) of 2,4-bis(4-dimethylamino-2-methylquinolin-6-yl)amino-6-chloro-[1,3,5]triazine prepared according to patent W0001561 and 1 ml (0.0078 mol) of N,N-dimethyl-1,3-propanediamine are successively loaded into a 250 ml round-bottomed flask containing 50 ml of DMF, with stirring, and then the mixture is heated for 15 hours at 100° C. The reaction medium is concentrated and taken up in 100 ml of water. The precipitate formed is filtered, washed with 2×50 ml of 0.1N NaOH and then dried. There are thus obtained 1.2 g of N,N'-bis(4-dimethylamino-2-methylquinolin-6-yl)-N"-(3-dimethylaminopropyl)-[1,3,5]triazine, which is purified by flash chromatography on 30 g of silica (35–70 $\mu$m), eluting with a mixture (85/10/5) of dichloromethane, methanol and triethylamine. There is thus obtained, after drying under vacuum at 40° C., 0.45 g (41%) of 2,4-bis(4-dimethylamino-2-methylquinolin-6-yl)amino-6-(3-dimethylaminopropyl)-amino-[1,3,5]triazine, in the form of a yellow powder whose characteristics are the following:

elemental analysis: % C=64.845 (cal=66.3); % H=6.855 (cal=7.13); % N=25.275 (cal=26.58);

$^1$H NMR spectrum (300 MHz, (CD$_3$)$_2$SO d6, $\delta$ in ppm): 1.73 (mt: 2H); 2.17 (s: 6H); 2.33 (broad t, J=7 Hz: 2H); 2.53 (broad s: 6H); 2.92 (unresolved complex: 12H); 3.43 (mt: 2H); 6.51 and 6.53 (2 broad s: 2H in total); 7.06 (unresolved complex: 1H); 7.51 (mt: 2H); from 8.10 to 8.30 (mt: 3H); 8.38 (unresolved complex: 1H); 9.24 (broad s: 1H); 9.37 (broad s: 1H).

EXAMPLES 1 TO 28

Examples 1 to 28 described in Table 1 may be prepared by parallel synthesis in liquid medium:

Into a heating magnetic reactor with a Zymark condenser, type STEM RS2050, containing 25 wells in parallel, provided with a 50 ml glass tube, there are introduced 50 mg of

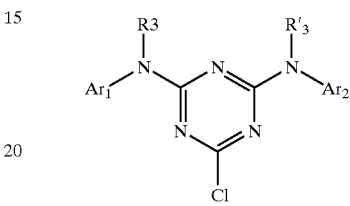

4 mole equivalents of R1-NH—R2 and 30 mg of potassium carbonate in 5 ml of DMF. The mixture is heated at 80° C. overnight. After cooling, the mixture is diluted with 30 ml of water and the precipitate obtained is filtered. The crude product thus isolated is generally clean (LC/MS purity>90%), it can however be purified by LC/MS using a Waters Xterra C18 silica column 3.5 $\mu$M, having a diameter of 3 mm and a length of 50 mm, eluting with a linear elution gradient consisting at the initial time (t0=0 min) of water supplemented with 0.05% of TFA and at the final time (tf=4 min) of acetonitrile containing 0.05% of TFA. Example 20 2,4-bis(4-dimethylamino-2-methylquinolin-6-yl)amino-6-(4-methylpiperazin-1-yl)-[1,3,5]triazine, may also be advantageously prepared in the following manner:

A solution containing 3 g of 4-dimethylamino-2-methylquinolin-6-amine, 2.75 g of 2,4,6-trichloro-s-triazine and 4 g of potassium carbonate in 300 ml of tetrahydrofuran is stirred overnight at room temperature, in a 1 l three-necked flask. The reaction medium is filtered, and then the filtrate is concentrated under reduced pressure; 5.1 g (98%) of 4,6-dichloro-2-(4-dimethylamino-2-methylquinolin-6-yl) amino-[1,3,5]triazine are thus obtained in the form of a brown solid whose characteristics are the following:

mass spectrum (EI/DCI)=349 (M+)

$^1$H NMR spectrum (300 MHz, (CD$_3$)$_2$SO d6, $\delta$ in ppm): 2.55 (s: 3 H); 3.01 (s: 6H); 6.78 (s: 1H); 7.68 (broad dd, J=9 and 2.5 Hz: 1H); 7.81 (d, J=9 Hz: 1H); 8.41 (unresolved complex: 1H); from 11.00 to 11.80 (broad unresolved complex: 1H).

The 5.1 g of 4,6-dichloro-2-(4-dimethylamino-2-methylquinolin-6-yl)amino-[1,3,5]triazine obtained above are dissolved, in a 1 l three-necked flask, in 500 ml of dioxane and then 2.94 g of 4-dimethylamino-2-methylquinolin-6-amine and 4 g of potassium carbonate are added. The reaction medium heated, with stirring, at the reflux temperature of dioxane for 16 hours, and then cooled and filtered, and then the filtrate is concentrated to dryness. 7.5 g (99%) of 6-chloro-2,4-bis(4-dimethylamino-2-methylquinolin-6-yl)amino-[1,3,5]triazine are thus obtained in the form of a brown solid whose characteristics are the following:

mass spectrum (EI/DCI)=514 (M+)

$^1$H NMR spectrum (400 MHz, (CD$_2$)$_3$SO d6 at a temperature of 383 K, $\delta$ in ppm): 2.57 (s: 6H); 2.95 (s: 12H);

6.72 (s: 2H); 7.77 (d, J=9 Hz: 2H); 7.94 (dd, J=9 and 2 Hz: 2H); 8.31 (d, J=2 Hz: 2H); 9.90 (unresolved complex: 2H).

The 7.5 g 6-chloro-2,4-bis(4-dimethylamino-2-methylquinolin-6-yl)amino-[1,3,5]triazine obtained above are dissolved, in a 500 ml three-necked flask, in 200 ml of dimethylformamide. 6 ml of 4-methylpiperazine and 4 g of potassium carbonate are then added. The reaction medium is then heated at 100–105° C. for 20 hours. After concentration under reduced pressure, the residue is precipitated from 200 ml of water. The crude product is then purified by flash chromatography on 300 g of silica (35–70 mesh), eluting with a mixture of dichloromethane, methanol and triethylamine (85/10/5 by volume). The fractions containing very predominantly the expected product are concentrated under reduced pressure, and then taken up in 60 ml of water, in order to remove the triethylamine. There are thus obtained, after drying, 3.1 (37%) of pure 2,4-bis(4-dimethylamino-2-methylquinolin-6-yl)amino-6-(4-methylpiperazin-1-yl)-[1,3,5]triazine in the form of a beige solid whose characteristics are the following:

melting point (Kofler stage)=256–60° C.

$^1$H NMR spectrum (400 MHz, (CD$_2$)$_3$SO d6 at a temperature of 383 K, δ in ppm): 2.30 (s: 3H); 2.47 (broad t, J=5 Hz: 4H); 2.55 (s: 6H); 2.94 (s: 12H); 3.89 (broad t, J=5 Hz: 4H); 6.75 (s: 2H); 7.74 (d, J=9 Hz: 2H); 7.99 (dd, J=9 and 2 Hz: 2H); 8.40 (d, J=2 Hz: 2H); from 8.70 to 9.00 (unresolved complex: 2H).

EXAMPLES 29 TO 33

Examples 29 to 33 described in Table 1 may be prepared by parallel synthesis in liquid medium:

2 mole equivalents of sodium hydride and 2 mole equivalents of R1OH in 5 ml of dioxane are introduced into a heating magnetic reactor with a Zymark condenser, type STEM RS2050, containing 25 wells in parallel provided with a 50 ml glass tube. The mixture is heated at 40° C. for 30 minutes. There are then added 50 mg of

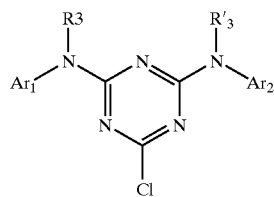

and the mixture is heated under reflux overnight. After cooling, the mixture is diluted with 30 ml of water and the precipitate obtained is filtered. The crude product thus isolated is purified by LC/MS using a Waters Xterra C18 silica column 3.5 μM, having a diameter of 3 mm and a length of 50 mm, eluting with a linear elution gradient consisting at the initial time (t0=0 min) of water supplemented with 0.05% of TFA and at the final time (tf=4 min) of acetonitrile containing 0.05% of TFA.

EXAMPLES 34 TO 102 may be obtained by carrying out the procedure as described above for Examples 1 to 28.

EXAMPLES 103 TO 115 may be obtained by carrying out the procedure as described above for Examples 29 to 33.

EXAMPLES 116 TO 133 may be obtained by carrying out the procedure as described above for Examples 29 to 33, but replacing R1OH with R1SH.

EXAMPLE 134 may be obtained by carrying out the procedure in the following manner:

In a 250 ml three-necked flask, there is dissolved, in 100 ml of dioxane, 1 g of 2,4-dichloro-6-phenyl-[1,3,5]triazine which may be obtained by carrying out the procedure according to Tetrahedron 2000, 56, 9705–9711. Next, 0.9 g of 4-dimethylamino-2-methylquinolin-6-amine and 1.2 g of potassium carbonate are added, and the reaction medium is heated at 80° C. for 18 hours. After cooling, the solvent is evaporated under reduced pressure and the residue is taken up in 100 ml of water. The precipitate formed is drained, washed with water and dried under reduced pressure. 1.5 g (89%) of 2-chloro-4-(4-dimethylamino-2-methylquinolin-6-yl)amino-6-phenyl-[1,3,5]triazine are thus obtained in the form of a yellow solid whose characteristics are the following:

mass spectrum (EI/DCI)=390 (M+)

$^1$H NMR spectrum (400 MHz, (CD$_3$)$_2$SO d6, at a temperature of 353 K, δ in ppm): 2.60 (s: 3H); from 2.95 to 3.10 (broad s: 6H); 6.83 (broad s: 1H); 7.62 (broad t, J=8 Hz: 2 H); 7.69 (broad t, J=8 Hz: 1H); 7.86 (d, J=9 Hz: 1H); 7.92 (broad dd, J=9 and 2 Hz: 1H); 8.43 (broad d, J=8 Hz: 2H); 8.70 (unresolved complex: 1H); 10.76 (unresolved complex: 1H).

0.39 g of 4-dimethylamino-2-methylquinolin-6-amine and 0.7 g of potassium carbonate are added to a solution of 0.75 g of 2-chloro-4-(4-dimethylamino-2-methylquinolin-6-yl)amino-6-phenyl-[1,3,5]triazine in 30 ml of DMF. Next, the reaction medium is heated for 18 hours at 140° C. After cooling and dilution with 100 ml of water, the precipitate formed is drained and then purified by flash chromatography on 50 g of silica gel (35–70 mesh), eluting with a mixture of dichloromethane, methanol and triethylamine (96/2/2 by volume). There is thus obtained 0.12 g (11%) of pure 2,4-bis(4-dimethylamino-2-methylquinolin-6-yl)amino-6-phenyl-[1,3,5]triazine in the form of a yellow solid whose characteristics are the following:

melting point (Kofler stage)=172° C.

$^1$H NMR spectrum (400 MHz, (CD$_3$)$_2$SO d6, with addition of a few drops of CD$_3$COOD d4, at a temperature of 353 K, δ in ppm): 2.51 (broad s: 6H); 3.20 (s: 12H); 6.76 (s: 2H); 7.55 (broad t, J=8 Hz: 2H); 7.60 (broad t, J=8 Hz: 1H); 7.87 (d, J=8.5 Hz: 2H); 8.30 (broad dd, J=8.5 and 2 Hz: 2H); 8.40 (broad d, J=8 Hz: 2H); 8.69 (d, J=2 Hz: 2H).

EXAMPLES 135 TO 176 may be obtained by carrying out the procedure as described above for Examples 1 to 28, except that the volume of DMF is reduced from 5 to 2 ml and that the heating temperature is increased from 80 to 108–110° C.

EXAMPLE 177

The G-quartet, antitelomerease and cytotoxic activities of the various exemplified compounds 1 to 176, given in Table 1, are determined according to the procedures described above.

TABLE 1

| Ar1 | R3 | Ar2 | R3 | X | R1 | R2 | G4 delta Tm °C. | TRAP IC50 μM | Cytotox. A549 IC50 μM | Ex # |
|---|---|---|---|---|---|---|---|---|---|---|
| 4-dimethylamino-2-methylquinolin-6-yl | H | 4-dimethylamino-2-methylquinolin-6-yl | H | N | 3-(dimethylamino)propyl | H | 11.3 | 0.55 | 0.23 | 1 |
| 4-amino-2-methylquinolin-6-yl | H | 4-amino-2-methylquinolin-6-yl | H | N | 4-amino-2-methylquinolin-6-yl | H | 18 | 0.06 | 10 | 2 |
| 4-amino-2-methylquinolin-6-yl | H | 4-dimethylamino-2-methylquinolin-6-yl | H | N | 2-chlorophenyl | H | 5.5 | 2.1 | 6 | 3 |
| 4-amino-2-methylquinolin-6-yl | H | 2-chlorophenyl | H | N | pyridin-4-yl | H | 5.5 | 3 | 4 | 4 |
| 4-amino-2-methylquinolin-6-yl | H | 2-chlorophenyl | H | N | 2-(dimethylamino)ethyl | H | 2.0 | 2.7 | | 5 |

TABLE 1-continued
| Ar1 | R3 | Ar2 | R3' | X | R1 | R2 | G4 delta Tm °C. | TRAP IC50 μM | Cytotox. A549 IC50 μM | Ex # |
|---|---|---|---|---|---|---|---|---|---|---|
| 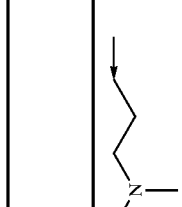 | H |  | H | N |  | H | | 3.5 | | 6 |
| 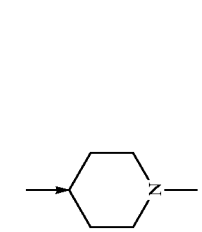 | H |  | H | N |  | H | 3.0 | 2.4 | | 7 |
| 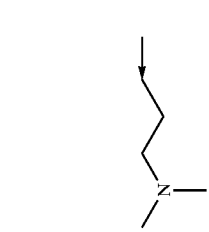 | H |  | H | N |  | H | 1.5 | 3.2 | | 8 |
| 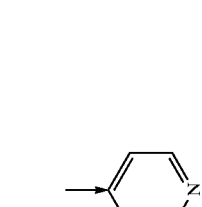 | H |  | H | N |  | H | 10.0 | 0.1 | | 9 |
|  | H |  | H | N |  | H | 8.9 | 0.36 | | 10 |

TABLE 1-continued
| Ar1 | R3 | Ar2 | R3' | X | R1 | R2 | G4 delta Tm °C. | TRAP IC50 µM | Cytotox. A549 IC50 µM | Ex # |
|---|---|---|---|---|---|---|---|---|---|---|
|  | H |  | H | N |  | H | 11.4 | 0.16 | | 11 |
| 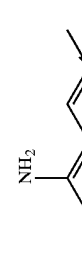 | H | 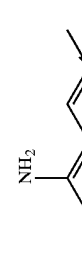 | H | N | 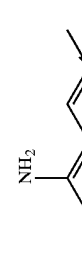 | H | 9.4 | 0.3 | | 12 |
| 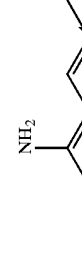 | H | 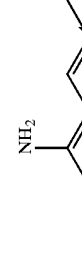 | H | N | 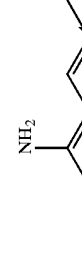 | H | 7.2 | 0.26 | | 13 |
| 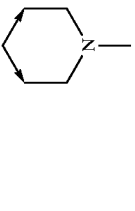 | H | 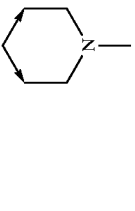 | H | N | 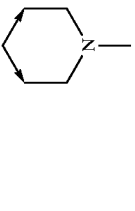 | H | 4.4 | 0.21 | | 14 |
| 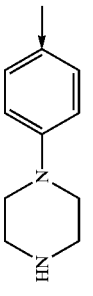 | H | 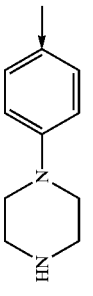 | H | N | 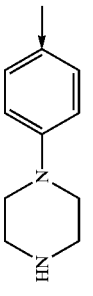 | H | 2.7 | 0.19 | 1.85 | 15 |

TABLE 1-continued

| Ar1 | R3 | Ar2 | R3' | X | R1 | R2 | G4 delta Tm °C. | TRAP IC50 μM | Cytotox. A549 IC50 μM | Ex # |
|---|---|---|---|---|---|---|---|---|---|---|
| 4-amino-2-methylquinoline | H | 4-amino-2-methylquinoline | H | N | pyrrolidin-2-ylmethyl | H | 7.3 | 0.08 | | 16 |
| 4-amino-2-methylquinoline | H | 4-amino-2-methylquinoline | H | N | quinuclidinyl | H | 17.1 | 0.1 | 2.73 | 17 |
| 4-dimethylamino-2-methylquinoline | H | 4-dimethylamino-2-methylquinoline | H | N | pyridin-4-yl | H | 2.4 | 1.2 | 2.86 | 18 |
| 4-dimethylamino-2-methylquinoline | H | 4-dimethylamino-2-methylquinoline | H | N | 1-methylpiperidin-4-yl | H | 3.5 | 0.53 | 0.3 | 19 |
| 4-dimethylamino-2-methylquinoline | H | 4-dimethylamino-2-methylquinoline | H | N | | 1-methylpiperidin-4-yl | 6.4 | 0.44 | 0.35 | 20 |

TABLE 1-continued
| Ar1 | R3 | Ar2 | R3' | X | R1 | R2 | G4 delta Tm °C | TRAP IC50 μM | Cytotox. A549 IC50 μM | Ex # |
|---|---|---|---|---|---|---|---|---|---|---|
|  | H |  | H | N |  | H | 11.0 | | | 21 |
|  | H |  | H | N |  | H | 2.7 | 0.34 | | 22 |
|  | H |  | H | N | |  | 9.2 | 3.0 | | 23 |
|  | H |  | H | N | |  | 9.7 | 1.6 | | 24 |
|  | H |  | H | N |  | H | 4.2 | 2.2 | | 25 |

TABLE 1-continued
| Ar1 | R3 | Ar2 | R3' | X | R1 | R2 | G4 delta Tm °C. | TRAP IC50 μM | Cytotox. A549 IC50 μM | Ex # |
|---|---|---|---|---|---|---|---|---|---|---|
| 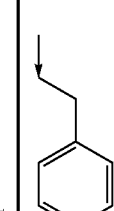 | H |  | H | N | 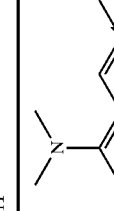 | H | 4.8 | 1.1 | | 26 |
| 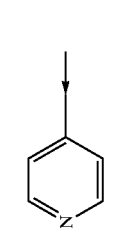 | H |  | H | N | 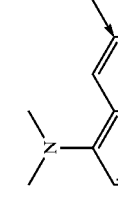 | H | 11.0 | 0.6 | 1.0 | 27 |
| 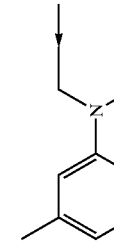 | H | 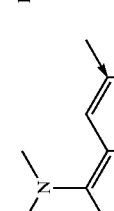 | H | N | 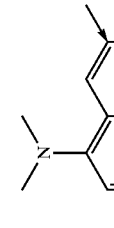 | H | 10.6 | 0.9 | 1.5 | 28 |
| 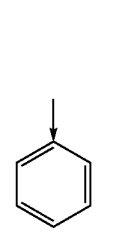 | H | 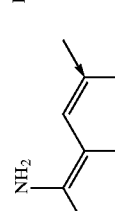 | H | O | 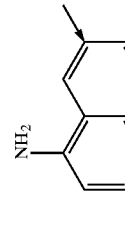 | no | 20.3<br>4.5 | 0.32<br>0.47 | | 29 |
| 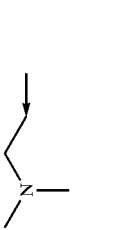 | H | 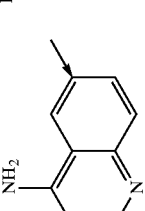 | H | O | 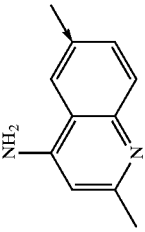 | no | 6.8<br>15.5 | 1.1<br>0.24 | | 30 |

TABLE 1-continued
| Ar1 | R3 | Ar2 | R3 | X | R1 | R2 | G4 delta Tm °C. | TRAP IC50 μM | Cytotox. A549 IC50 μM | Ex # |
|---|---|---|---|---|---|---|---|---|---|---|
| 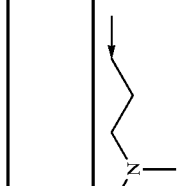 | H | 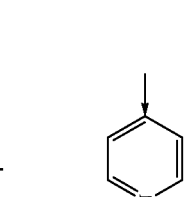 | H | O | 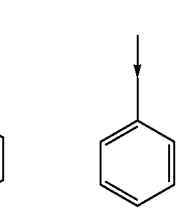 | no | 15.3 | 0.3 | | 31 |
| 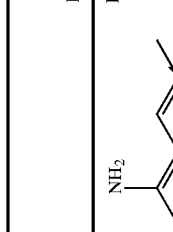 | H | 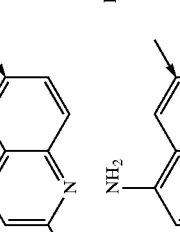 | H | O | 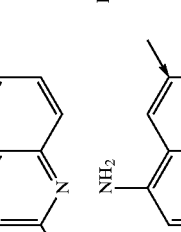 | no | 10.0 | 0.3 | | 32 |
| 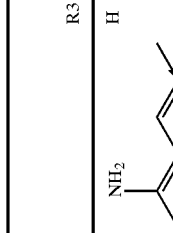 | H | 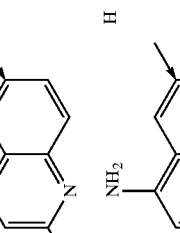 | H | O | 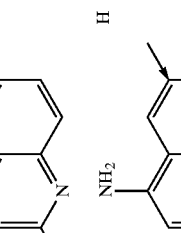 | no | 10.0 | 0.4 | | 33 |
| 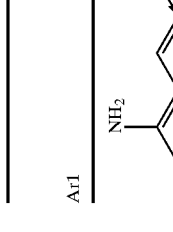 | H | 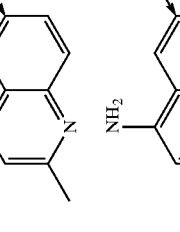 | H | N | | 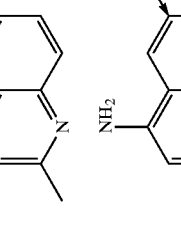 | 5.0 | 0.68 | 15 | 34 |
| 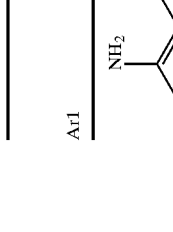 | H | 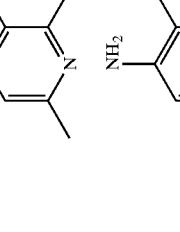 | H | N | 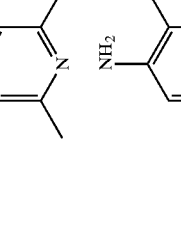 | H | 11.0 | 0.5 | | 35 |
| 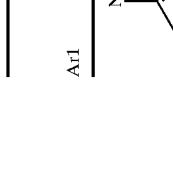 | H | 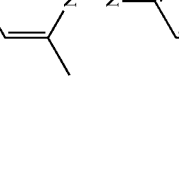 | H | N | 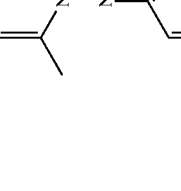 | H | 17.5 | 0.24 | | 36 |

TABLE 1-continued

| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 4-NH₂-2-methylquinolin-6-yl | H | 4-NH₂-2-methylquinolin-6-yl | H | N | N-benzyl-N-(2-dimethylaminoethyl) | H | 17.5 | 0.23 | | 37 |
| 4-NH₂-2-methylquinolin-6-yl | H | 4-NH₂-2-methylquinolin-6-yl | H | N | methoxycarbonylaminomethyl | H | 9.5 | 1.0 | | 38 |
| 4-NH₂-2-methylquinolin-6-yl | H | 4-NH₂-2-methylquinolin-6-yl | H | N | diisopropylaminomethyl | H | 19.5 | 0.23 | | 39 |
| 4-NH₂-2-methylquinolin-6-yl | H | 4-NH₂-2-methylquinolin-6-yl | H | N | diethylaminomethyl | diethylaminomethyl | 19 | 0.23 | | 40 |
| 4-NH₂-2-methylquinolin-6-yl | H | 4-NH₂-2-methylquinolin-6-yl | H | N | 1-benzylpyrrolidin-3-yl | H | 19 | 0.36 | 9.9 | 41 |

TABLE 1-continued
| Ar1 | R3 | Ar2 | R'3 | X | R1 | R2 | G4 delta Tm °C. | TRAP IC50 µM | Cytotox. A549 IC50 µM | Ex # |
|---|---|---|---|---|---|---|---|---|---|---|
| 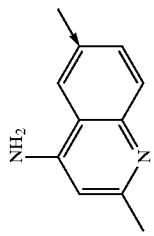 | H | 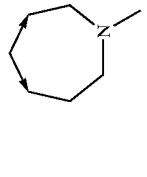 | H | N | | 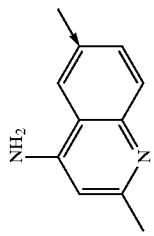 | 15.5 | 0.05 | | 42 |
| 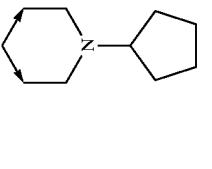 | H | 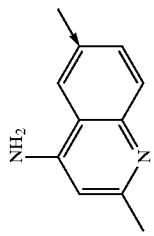 | H | N | | 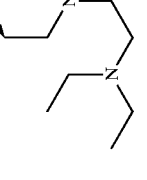 | 18 | 0.18 | 10 | 43 |
| 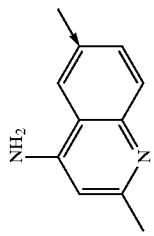 | H |  | H | N | | 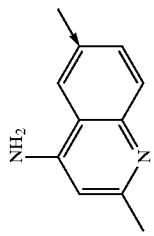 | 17 | 0.1 | | 44 |
|  | H | 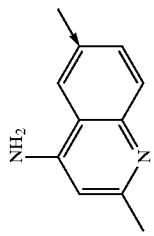 | H | N | 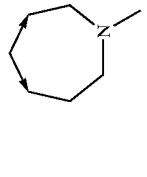 | H | 16.5 | 0.33 | | 45 |
| 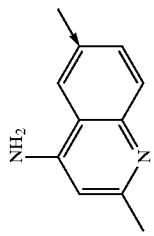 | H | 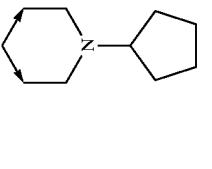 | H | N | | H | 18.5 | 1 | | 46 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 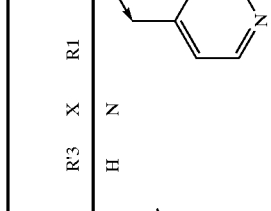 | H | 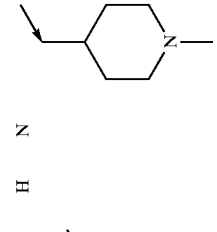 | H | N | 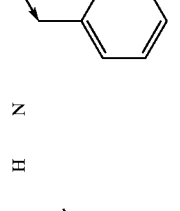 | H | 8 | 0.2 | | 47 |
| 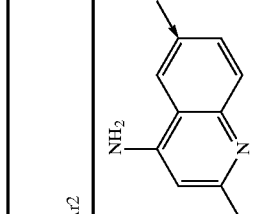 | H | 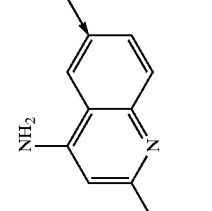 | H | N | 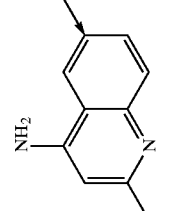 | Me | 14 | 0.1 | | 48 |
| 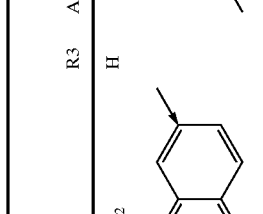 | H | 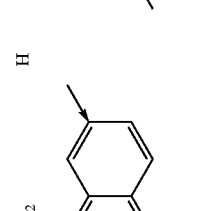 | H | N | 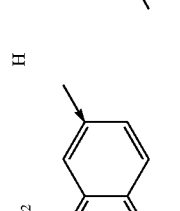 | H | 10 | 1 | | 49 |
| 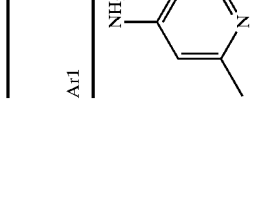 | H | 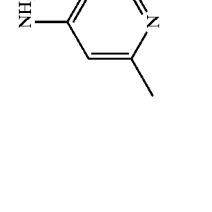 | H | N | 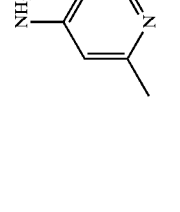 | H | 7 | 0.22 | | 50 |
| 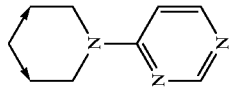 | H | | H | N | |  | 11 | 0.26 | | 51 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 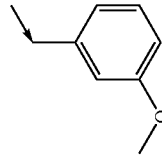 | H | 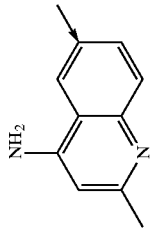 | H | N | 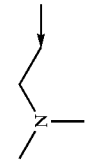 | H | 6.5 | 1.3 | | 52 |
| 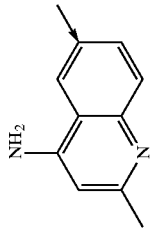 | H | 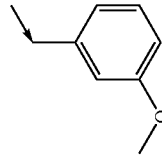 | H | N | 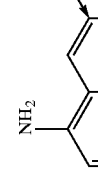 | Et | 15.5 | 0.2 | | 53 |
| 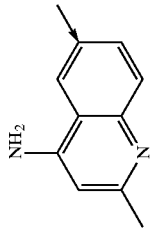 | H | 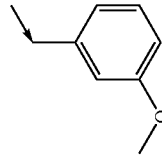 | H | N | 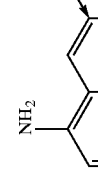 | H | 16 | 0.17 | | 54 |
| 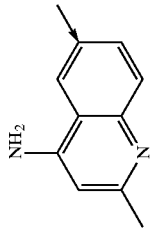 | H | 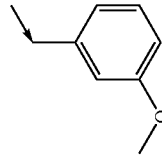 | H | N | | 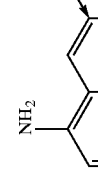 | 15.5 | 0.21 | | 55 |
| 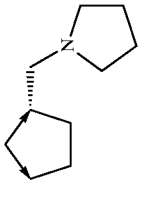 | H | 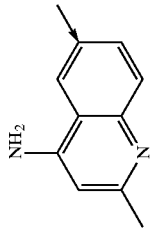 | H | N | 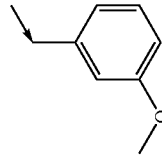 | H | 2.5 | 0.35 | | 56 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 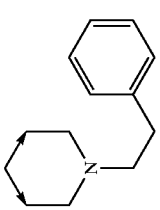 | H | 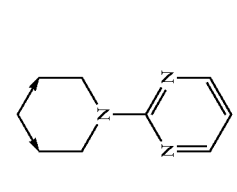 | H | N | | 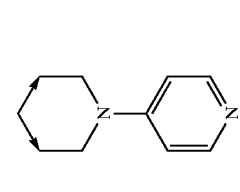 | 8 | 0.3 | | 57 |
|  | H | 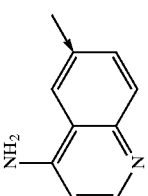 | H | N | | 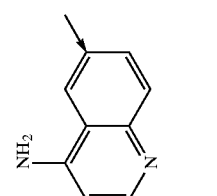 | 6 | 0.22 | | 58 |
| 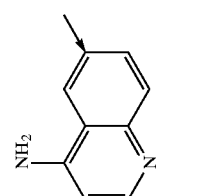 | H | 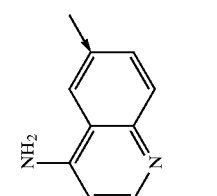 | H | N | | 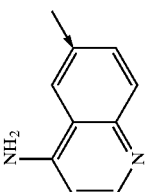 | 11 | 0.19 | | 59 |
| 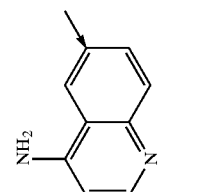 | H | 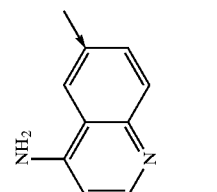 | H | N | | H | 6 | 3.0 | 5.7 | 60 |
Example 60, R1: aryl trimethylammonium chloride substituent TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
|  | H | 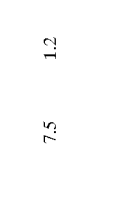 | H | N |  | H | | 0.36 | | 61 |
|  | H |  | H | N |  | H | 7.5 | 1.2 | | 62 |
| 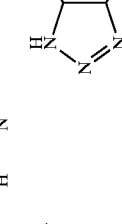 | H | 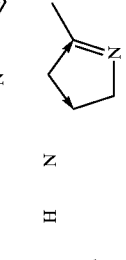 | H | N | 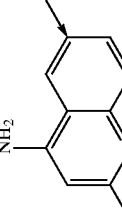 | Me | 11.5 | 0.19 | | 63 |
| 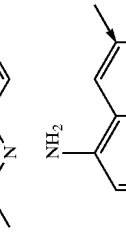 | H | 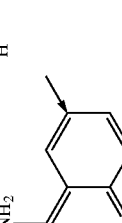 | H | N | 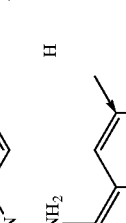 | 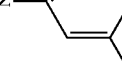 | 12 | 0.09 | | 64 |
|  | H | | H | N | | Me | 12.5 | 1 | | 65 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
|  | H |  | H | N |  |  | 9 | 0.28 |  | 66 |
|  | H |  | H | N |  |  | 6.5 | 0.43 |  | 67 |
|  | H |  | H | N |  |  | 8 | 0.3 | 11.5 | 68 |
| 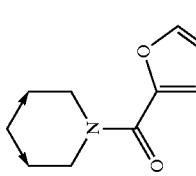 | H | 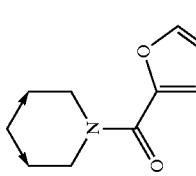 | H | N |  | 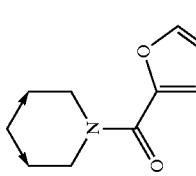 | 18 | 0.16 |  | 69 |
| 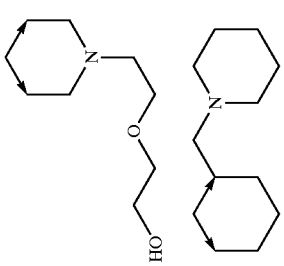 | H | 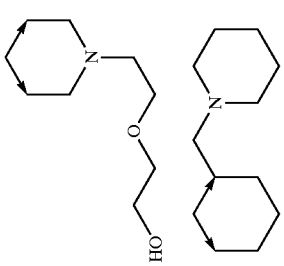 | H | N |  | 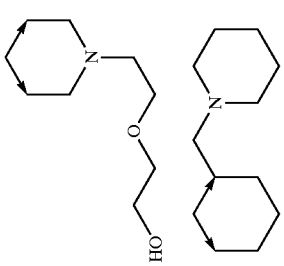 | 9.5 | 0.56 |  | 70 |

TABLE 1-continued

| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 4-amino-2-methylquinoline | H | 4-amino-2-methylquinoline | H | N | | piperidinyl-quinoline | | 0.35 | 12.4 | 71 |
| 4-amino-2-methylquinoline | H | 4-amino-2-methylquinoline | H | N | | piperidinyl-(tetrahydrofuran-2-yl)carbonyl | 9.5 | 0.21 | | 72 |
| 4-amino-2-methylquinoline | H | 4-amino-2-methylquinoline | H | N | | piperidinyl-(2-methoxyethyl) | 9.5 | 0.37 | | 73 |
| 4-amino-2-methylquinoline | H | 4-amino-2-methylquinoline | H | N | H | 4-benzylpiperazinyl-ethyl | 9.5 | 0.14 | | 74 |

TABLE 1-continued
| Ar1 | R3 | Ar2 | R'3 | X | R1 | R2 | G4 delta Tm ° C. | TRAP IC50 μM | Cytotox. A549 IC50 μM | Ex # |
|---|---|---|---|---|---|---|---|---|---|---|
| 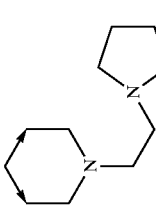 | H |  | H | N | | 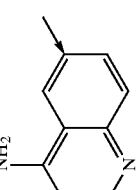 | 13.5 | 0.05 | | 75 |
| 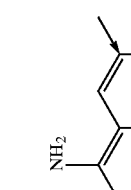 | H | 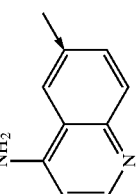 | H | N | | 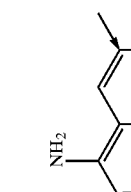 | 19 | 0.11 | | 76 |
|  | H | 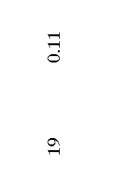 | H | N | |  | 12.5 | 0.48 | 5.6 | 77 |
|  | H | | H | N |  | H | | 1.5 | | 78 |
| | H | | H | N |  | H | | 3.6 | | 79 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 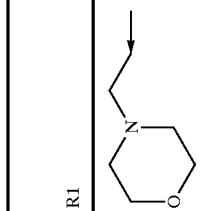 | H | 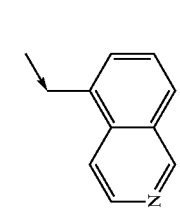 | H | N | 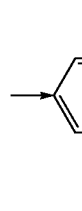 | H | | 1.2 | | 80 |
| 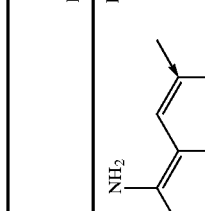 | H | 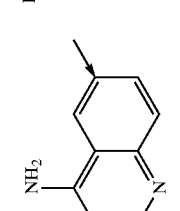 | H | N |  | H | | 1.4 | | 81 |
| 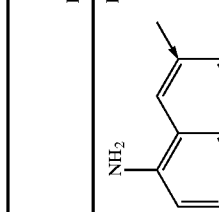 | H | 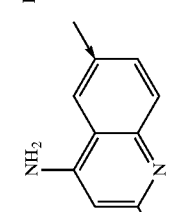 | H | N |  | H | | 1.6 | | 82 |
| 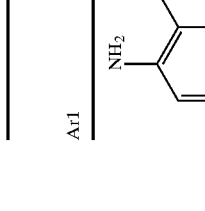 | H | 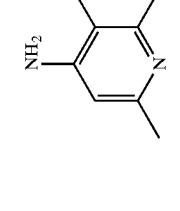 | H | N |  | H | | 1.2 | 14 | 83 |
| 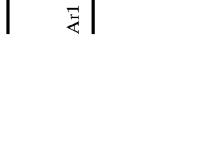 | H |  | H | N |  | H | | 2.2 | | 84 |

TABLE 1-continued

| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 4-amino-2-methylquinoline | H | 4-amino-2-methylquinoline | H | N | 4-(dimethylamino)benzyl | H |  | 3.9 | 16 | 85 |
| 4-amino-2-methylquinoline | H | 4-amino-2-methylquinoline | H | N |  | 3-(pyridin-3-yl)cyclopentyl | 6 | 0.2 | 18.9 | 86 |
| 4-amino-2-methylquinoline | H | 4-amino-2-methylquinoline | H | N | isoquinolin-1-ylmethyl | H |  | 1.5 | 87 | 87 |
| 4-amino-2-methylquinoline | H | 4-amino-2-methylquinoline | H | N |  | 2-(4-methylpiperazin-1-yl)ethyl-N-methyl | 6 | 0.11 |  | 88 |
| 4-amino-2-methylquinoline | H | 4-amino-2-methylquinoline | H | N | pyridin-2-ylmethyl | H |  | 1.2 | 20 | 89 |

TABLE 1-continued
| Ar1 | R3 | Ar2 | R3 | X | R1 | R2 | G4 delta Tm °C | TRAP IC50 μM | Cytotox. A549 IC50 μM | Ex # |
|---|---|---|---|---|---|---|---|---|---|---|
| 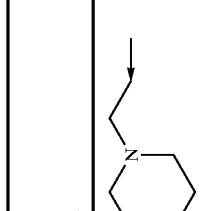 | H | 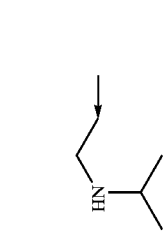 | H | N |  | H | 11 | 0.37 | | 90 |
| 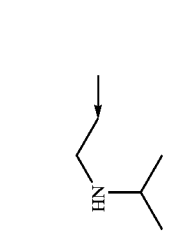 | H | 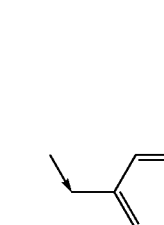 | H | N | 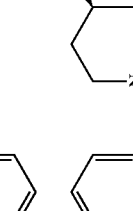 | H | 7 | 0.37 | | 91 |
| 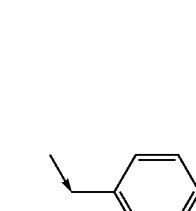 | H | 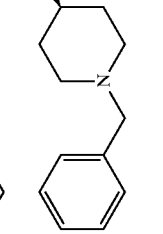 | H | N | 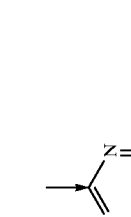 | 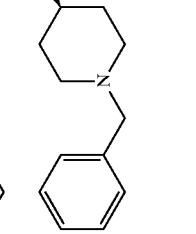 | 3.5 | 0.43 | 7.8 | 92 |
|  | H | 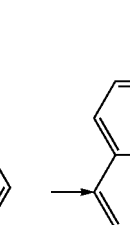 | H | N | 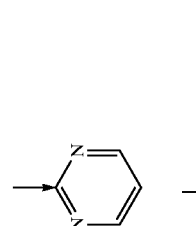 | H | 8 | 0.37 | 9.3 | 93 |
| 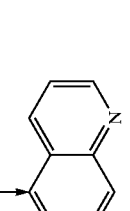 | H |  | H | N | 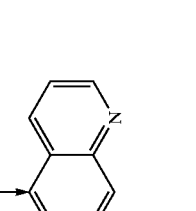 | H | | 0.94 | | 94 |
|  | H |  | H | N | | H | | 0.93 | | 95 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 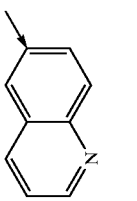 | H | 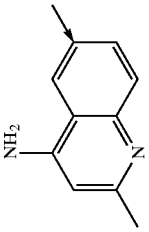 | H | N | 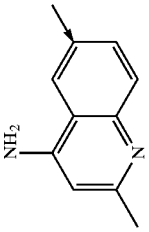 | H | | 0.48 | | 96 |
| 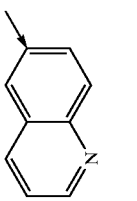 | H | 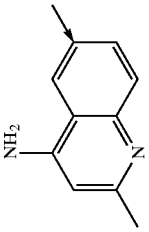 | H | N | 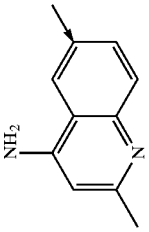 | H | | 0.69 | | 97 |
| 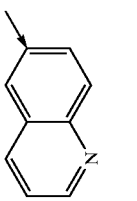 | H | 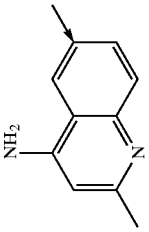 | H | N | 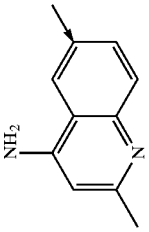 | H | 4 | 0.35 | | 98 |
| 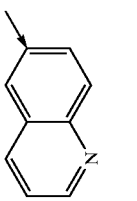 | H | 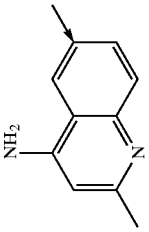 | H | N | 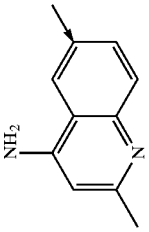 | H | | 0.6 | | 99 |
| | H | | H | N | | H | | 0.45 | | 100 |

TABLE 1-continued

| Ar1 | R3 | Ar2 | R3 | X | R1 | R2 | G4 delta Tm °C. | TRAP IC50 µM | Cytotox. A549 IC50 µM | Ex # |
|---|---|---|---|---|---|---|---|---|---|---|
| 4-NH2-2-methylquinoline | H | 4-NH2-2-methylquinoline | H | N | 5-isoquinolinyl | H | | 0.81 | | 101 |
| 4-NH2-2-methylquinoline | H | 4-NH2-2-methylquinoline | H | N | 6-ethoxy-8-quinolinyl | H | | 0.57 | | 102 |
| 4-NH2-2-methylquinoline | H | 4-NH2-2-methylquinoline | H | O | 2-chlorophenyl | no | 7 | 0.28 | 11.34 | 103 |
| 4-NH2-2-methylquinoline | H | 4-NH2-2-methylquinoline | H | O | 3-methoxyphenyl | no | 4.5 | 1.2 | 11.37 | 104 |
| 4-NH2-2-methylquinoline | H | 4-NH2-2-methylquinoline | H | O | N-methyl-N-benzyl-aminoethyl | no | 12 | 0.24 | 11.57 | 105 |
| 4-NH2-2-methylquinoline | H | 4-NH2-2-methylquinoline | H | O | N,N-diethyl-aminoethyl | no | 14.5 | 0.28 | | 106 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 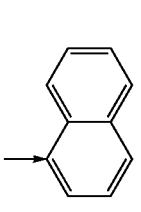 | H | 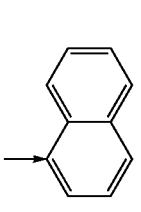 | H | O | 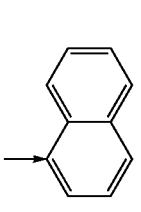 | no | 4.5 | 0.37 | | 107 |
| 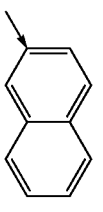 | H | 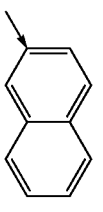 | H | O | 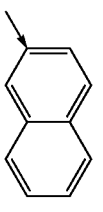 | no | 3 | 0.37 | | 108 |
| 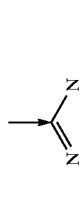 | H | 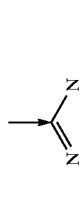 | H | O | 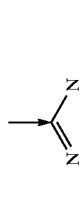 | no | 4.5 | 0.34 | | 109 |
|  | H |  | H | O |  | no | 20.5 | 0.61 | | 110 |
|  | H |  | H | O |  | no | 23.5 | 0.48 | | 111 |
| 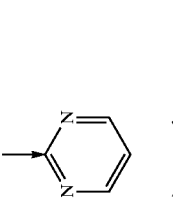 | H | 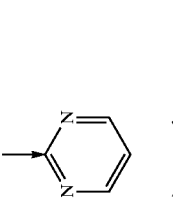 | H | O |  | no | 15 | 0.32 | | 112 |

TABLE 1-continued
| Ar1 | R3 | Ar2 | R'3 | X | R1 | R2 | G4 delta Tm °C. | TRAP IC50 µM | Cytotox. A549 IC50 µM | Ex # |
|---|---|---|---|---|---|---|---|---|---|---|
|  | H | 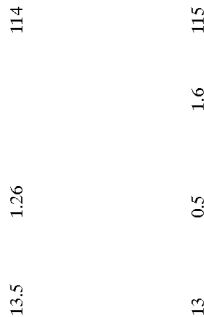 | H | O |  | no | 6 | 0.53 | | 113 |
|  | H | 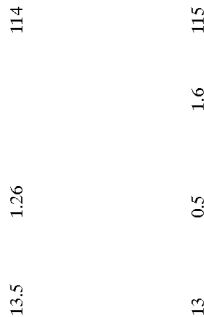 | H | O | 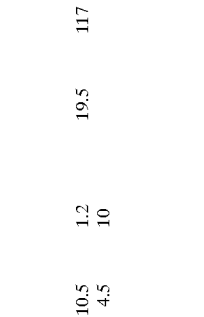 | no | 13.5 | 1.26 | | 114 |
|  | H | 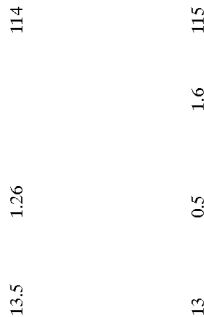 | H | O |  | no | 13 | 0.5 | | 115 |
|  | H | 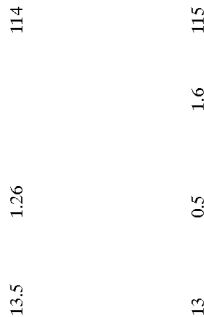 | H | S |  | no | | 1.8 | 1.6 | 116 |
|  | H | 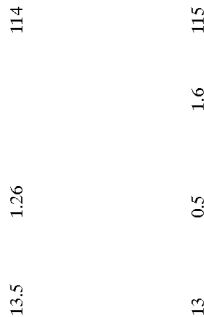 | H | S | | no | 10.5 4.5 | 1.2 10 | 19.5 | 117 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 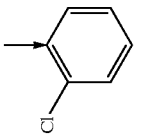 | H | 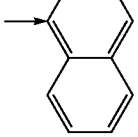 | H | S | 2-chlorophenyl | no | 3.5 | 1.4 | 13.7 | 118 |
| 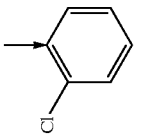 | H | 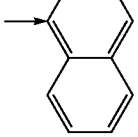 | H | S | 1-naphthyl | no | 4.5 | | | 119 |
| 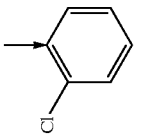 | H | 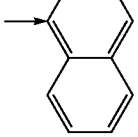 | H | S | 2-pyridyl | no | 11.5 | 0.38 | 17.8 | 120 |
| 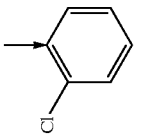 | H | 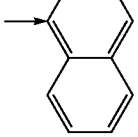 | H | S | 2-pyrimidyl | no | 4.5 / 12.5 | 0.4 / 0.36 | | 121 |
| 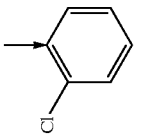 | H | 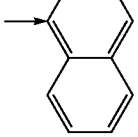 | H | S | 3-methoxyphenyl | no | 13.5 | 0.37 | | 122 |
| 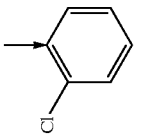 | H | 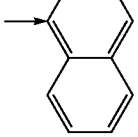 | H | S | benzyl | no | 3 | 1.3 | 11.6 | 123 |

TABLE 1-continued
| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 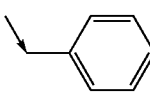 | H | 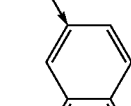 | H | S | 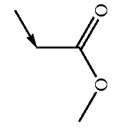 | no | 3 | 0.9 | 6.2 | 124 |
| 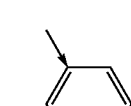 | H |  | H | S | 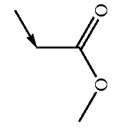 | no | 14.5 | 0.36 | | 125 |
| 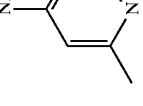 | H | 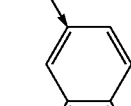 | H | S | 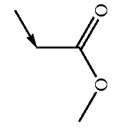 | no | 19 | 0.67 | 11.4 | 126 |
| 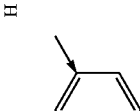 | H | 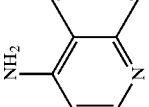 | H | S | 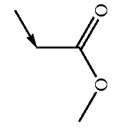 | no | 14 | 0.84 | 15.9 | 127 |
| 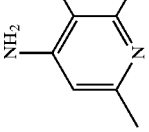 | H |  | H | S | 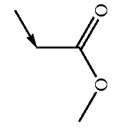 | no | 15 | 0.39 | 2.86 | 128 |

TABLE 1-continued
| Ar1 | R3 | Ar2 | R3' | X | R1 | R2 | G4 delta Tm °C. | TRAP IC50 µM | Cytotox. A549 IC50 µM | Ex # |
|---|---|---|---|---|---|---|---|---|---|---|
| 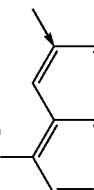 | H | 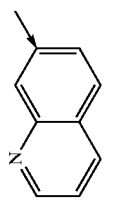 | H | S | 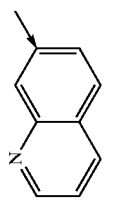 | no | 15.5 | 0.82 | | 129 |
| 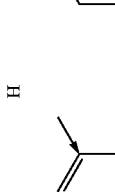 | H | 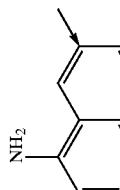 | H | S | 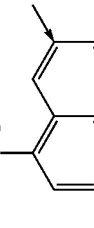 | no | 9 | 0.3 | | 130 |
| 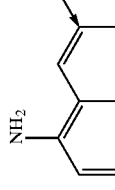 | H | 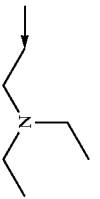 | H | S |  | no | 4.5 | 0.91 | | 131 |
|  | H | 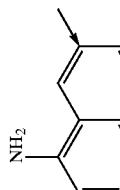 | H | S | 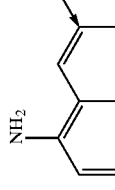 | no | 12.5 | 0.4 | | 132 |
| 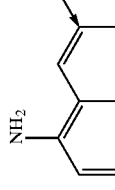 | H | 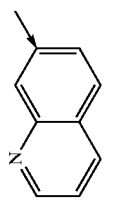 | H | S |  | no | 25 | 0.18 | | 133 |

TABLE 1-continued
| Ar1 | R3 | Ar2 | R'3 | X | R1 | R2 | G4 delta Tm °C. | TRAP IC50 µM | Cytotox. A549 IC50 µM | Ex # |
|---|---|---|---|---|---|---|---|---|---|---|
| 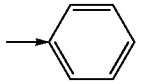 | H | 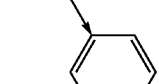 | H | no | | no | 8 | 0.3 | 0.88 | 134 |
| 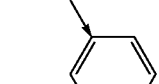 | H | 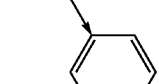 | H | N | 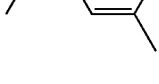 | 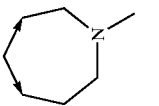 | 20 | 0.4 | 0.07 | 135 |
| 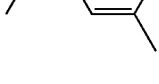 | H | 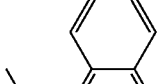 | H | N | |  | 20.5 | 0.12 | 0.026 | 136 |
| 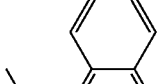 | H |  | H | N | | 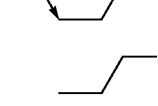 | 16 | 1 | 0.15 | 137 |
|  | H |  | H | N |  | Me | 16 | 0.5 | 0.061 | 138 |

TABLE 1-continued
| Ar1 | R3 | Ar2 | R3' | X | R1 | R2 | G4 delta Tm °C. | TRAP IC50 μM | Cytotox. A549 IC50 μM | Ex # |
|---|---|---|---|---|---|---|---|---|---|---|
| 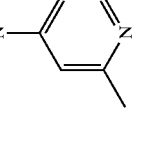 | H | 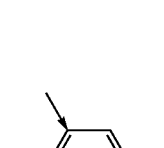 | H | N | | 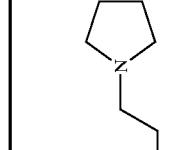 | 18.5 | 0.6 | 0.045 | 139 |
| 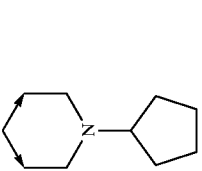 | H | 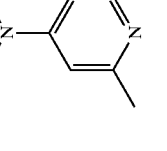 | H | N | 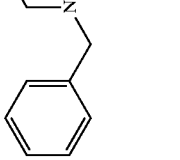 | H | 5.5 | 1 | 0.512 | 140 |
|  | H |  | H | N | | 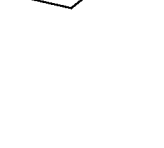 | 7 | 0.9 | 0.096 | 141 |
| 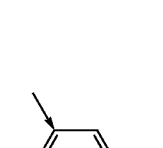 | H | 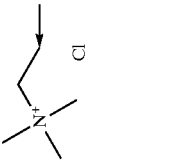 | H | N | 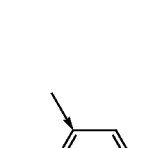 | H | 9.5 | 1 | 1.56 | 142 |
| 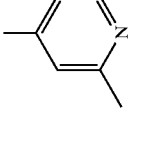 | H | 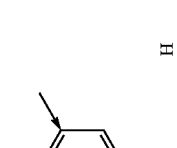 | H | N | | 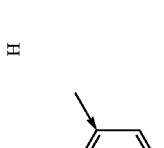 | 13 | 0.4 | 0.52 | 143 |

TABLE 1-continued
| Ar1 | R3 | Ar2 | R3' | X | R1 | R2 | G4 delta Tm °C. | TRAP IC50 μM | Cytotox. A549 IC50 μM | Ex # |
|---|---|---|---|---|---|---|---|---|---|---|
| 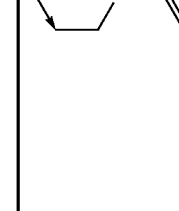 | H | 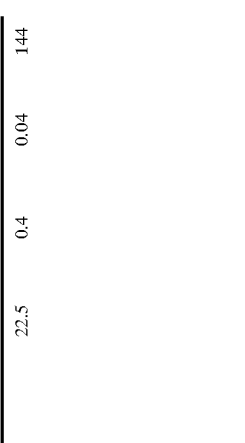 | H | N | | | 22.5 | 0.4 | 0.04 | 144 |
| 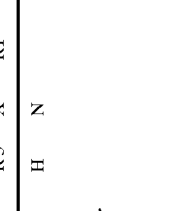 | H | 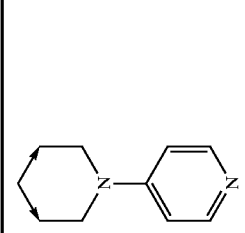 | H | N | 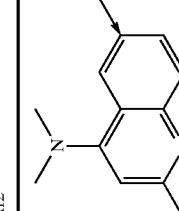 | H | 5 | 1 | 0.42 | 145 |
| 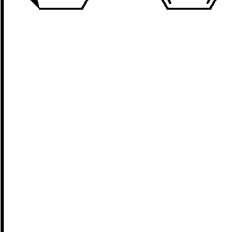 | H | 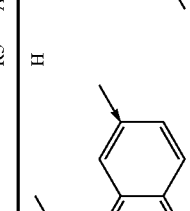 | H | N | 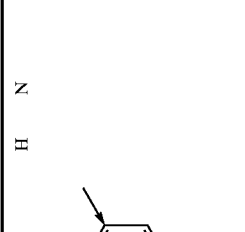 | Et | 6 | 0.6 | 0.175 | 146 |
| 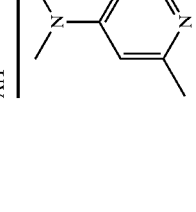 | H | 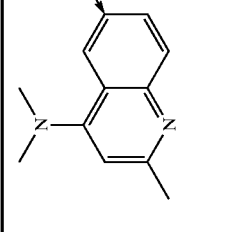 | H | N | | 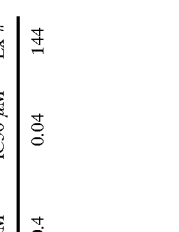 | | 1 | 0.21 | 147 |
| 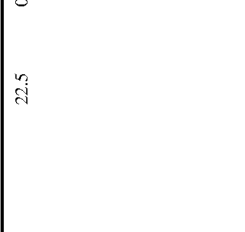 | H | 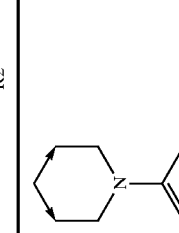 | H | N | |  | 12 | 1.5 | 1.5 | 148 |

TABLE 1-continued

| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| (dimethylamino-methylquinoline) | H | (dimethylamino-methylquinoline) | H | N |  | pyrrolidinylmethyl-cyclopentyl | 12.5 | 2.5 | 0.096 | 149 |
| (dimethylamino-methylquinoline) | H | (dimethylamino-methylquinoline) | H | N | acetamidoethyl | H | 6.5 | 2.5 | 2.47 | 150 |
| (amino-methylquinoline) | H | (amino-methylquinoline) | H | N |  | acetamido-cyclopentyl | 6.5 | 0.38 |  | 151 |
| (amino-methylquinoline) | H | (amino-methylquinoline) | H | N | hydroxyethyl | hydroxyethyl | 9.5 | 0.47 |  | 152 |
| (amino-methylquinoline) | H | (amino-methylquinoline) | H | N |  | hydroxycyclopentyl | 10 | 0.41 |  | 153 |

TABLE 1-continued

| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 4-amino-2-methylquinoline (6-subst) | H | 4-amino-2-methylquinoline (6-subst) | H | N | | piperidine-N-CH2CH2OH | 19 | 0.2 | | 154 |
| 4-amino-2-methylquinoline (6-subst) | H | 4-amino-2-methylquinoline (6-subst) | H | N | | cyclohexanol | 14 | 0.39 | | 155 |
| 4-amino-2-methylquinoline (6-subst) | H | 4-amino-2-methylquinoline (6-subst) | H | N | CH3CH(OMe)CH3 | H | 14.5 | 1.2 | | 156 |
| 4-amino-2-methylquinoline (6-subst) | H | 4-amino-2-methylquinoline (6-subst) | H | N | CH3CH2CH(CH2OH) | H | 12.5 | 1.4 | | 157 |
| 4-amino-2-methylquinoline (6-subst) | H | 4-amino-2-methylquinoline (6-subst) | H | N | HOCH2CH2 | H | 8 | 0.85 | | 158 |
| 4-amino-2-methylquinoline (6-subst) | H | 4-amino-2-methylquinoline (6-subst) | H | N | | cyclopentyl-CH2OMe | 10.5 | 0.43 | | 159 |

TABLE 1-continued

| Ar1 | R3 | Ar2 | R'3 | X | R1 | R2 | G4 delta Tm °C. | TRAP IC50 μM | Cytotox. A549 IC50 μM | Ex # |
|---|---|---|---|---|---|---|---|---|---|---|
| 4-amino-2-methylquinolin-6-yl | H | 4-amino-2-methylquinolin-6-yl | H | N | | 3-hydroxycyclohexyl | 10.5 | 0.36 | | 160 |
| 4-dimethylamino-2-methylquinolin-6-yl | H | 4-dimethylamino-2-methylquinolin-6-yl | H | N | 2-hydroxyethyl | 2-hydroxyethyl | 12 | 1.9 | | 161 |
| 4-dimethylamino-2-methylquinolin-6-yl | H | 4-dimethylamino-2-methylquinolin-6-yl | H | N | | 3-hydroxycyclopentyl | 17 | 1.7 | | 162 |
| 4-dimethylamino-2-methylquinolin-6-yl | H | 4-dimethylamino-2-methylquinolin-6-yl | H | N | | 2-(4-piperidinyl)ethanol-N-yl | 13 | 1.2 | | 163 |
| 4-dimethylamino-2-methylquinolin-6-yl | H | 4-dimethylamino-2-methylquinolin-6-yl | H | N | | 4-hydroxycyclohexyl | 12.5 | 1.6 | | 164 |

TABLE 1-continued
| Ar1 | R3 | Ar2 | R3 | X | R1 | R2 | G4 delta Tm °C. | TRAP IC50 μM | Cytotox. A549 IC50 μM | Ex # |
|---|---|---|---|---|---|---|---|---|---|---|
| 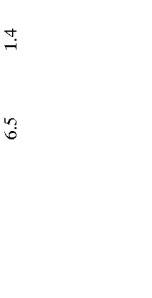 | H |  | H | N |  | H | 6.5 | 1.4 | | 165 |
|  | H |  | H | N |  | H | 12.5 | 1.4 | | 166 |
| 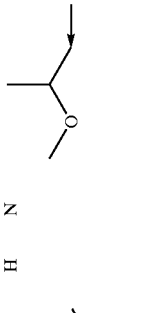 | H | 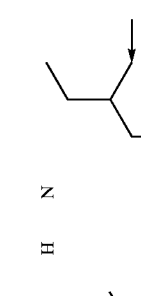 | H | N | 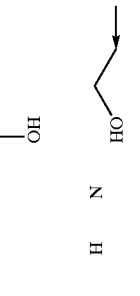 | H | 6 | 1.1 | | 167 |
| 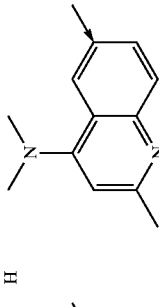 | H | 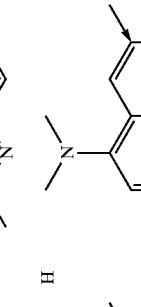 | H | N | | 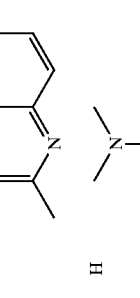 | 16.5 | 1.1 | | 168 |
| 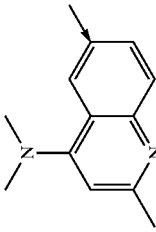 | H | 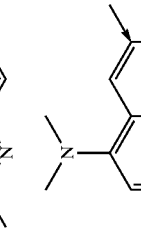 | H | N | | 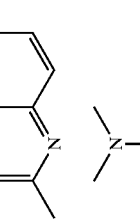 | 16.5 | 0.7 | | 169 |

TABLE 1-continued
| Ar1 | R3 | Ar2 | R3 | X | R1 | R2 | G4 delta Tm °C. | TRAP IC50 μM | Cytotox. A549 IC50 μM | Ex # |
|---|---|---|---|---|---|---|---|---|---|---|
| 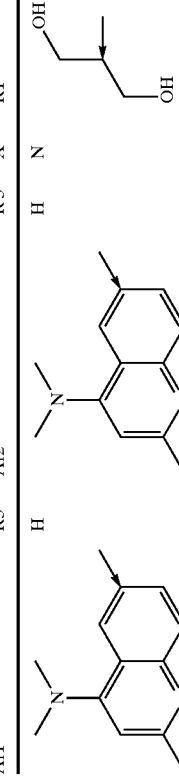 | H | 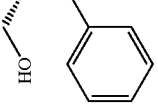 | H | N | 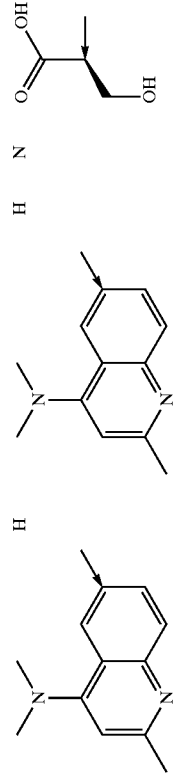 | H | 3 | 1.3 | | 170 |
| 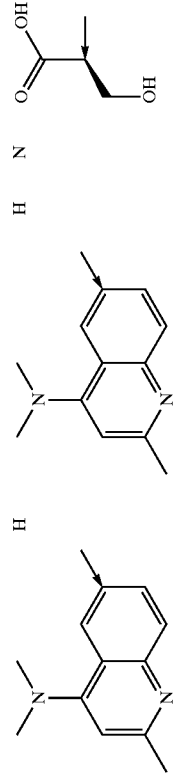 | H | 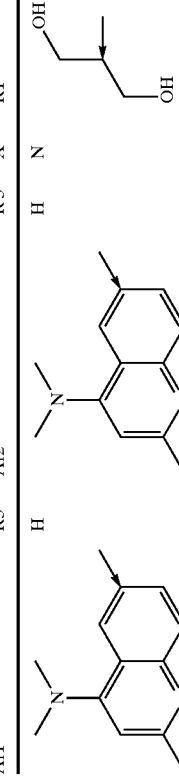 | H | N | 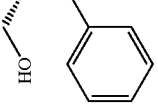 | H | 13 | 0.49 | | 171 |
| 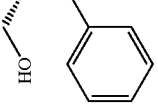 | H | 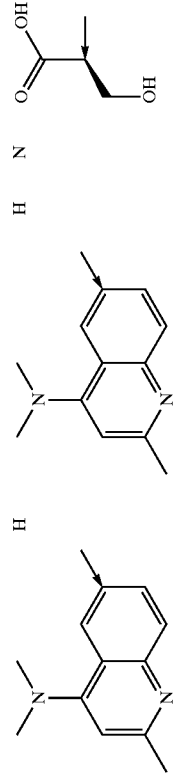 | H | N | 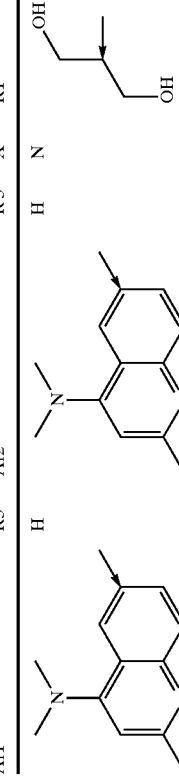 | H | 20 | 0.33 | | 172 |
| 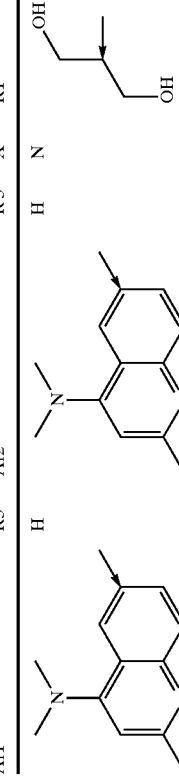 | H | 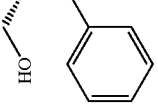 | H | N | 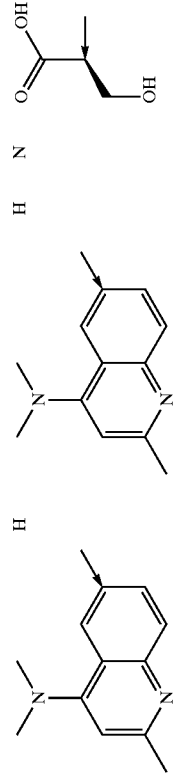 | H | 11.5 | 0.62 | | 173 |

TABLE 1-continued
| Ar1 | R3 | Ar2 | R3' | X | R1 | R2 | G4 delta Tm °C. | TRAP IC50 μM | Cytotox. A549 IC50 μM | Ex # |
|---|---|---|---|---|---|---|---|---|---|---|
| 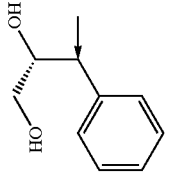 | H | 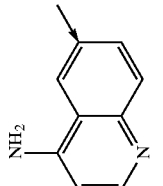 | H | N | 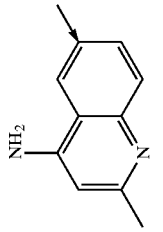 | H | 6 | 0.26 | | 174 |
| 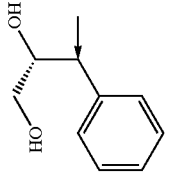 | H | 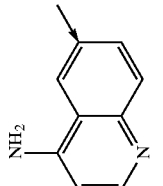 | H | N | 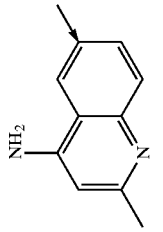 | H | 3 | 3 | | 175 |
| 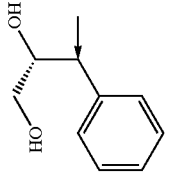 | H | 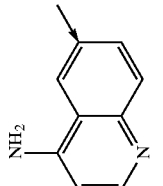 | H | N | 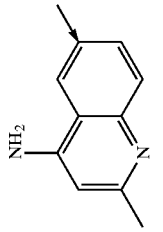 | H | 6 | 3 | | 176 |

What is claimed is:

1. A compound which binds a G-quadruplex structure of DNA or RNA, wherein the compound corresponds to the following formula:

nitrogen-containing aromatic ring—$NR_3$—distribution agent—$NR'_3$—aromatic ring in which:
the nitrogen-containing aromatic ring represents:
  a quinolinyl or isoquinolinyl radical optionally substituted with at least one radical chosen from among:
    N(Ra)(Rb), wherein Ra and Rb are identical or different and represent hydrogen or C1–C4 alkyl radical, and
    a short-chain C1–C4 alkoxy or alkyl group,
  a quinolinyl or isoquinolinyl radical possessing a nitrogen atom in quaternary form, or
  a pyridinyl radical;
or wherein the nitrogen-containing ring is replaced by a benzimidinyl radical;
the aromatic ring represents:
  a quinolinyl radical optionally substituted with at least one radical chosen from among:
    N(Ra)(Rb), wherein Ra and Rb are identical or different and represent hydrogen or C1–C4 alkyl radical, and a short-chain C1–C4 alkoxy or alkyl group,
  a quinolinyl radical possessing a nitrogen atom in quaternary form,
  a benzamidinyl radical,
  a pyridinyl radical,
  a phenyl ring optionally substituted with a halogen chosen from iodine, bromine or fluorine, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group for each alkyl, C1–C4 dialkylamino group for each alkyl in which the alkyl portions together form a C3–C8 ring, nitro group, C1–C4 alkyleneamino group, or C2–C4 alkenyleneamino group, or
  a mono- or bi- or tricyclic heterocyclic ring comprising 0 to 2 heteroatoms per ring wherein at least one heteroatom is present in at least one ring that is optionally substituted with one or more C1–C4 alkyl groups, C1–C4 alkylene groups, or C2–C4 alkenylene groups;
R3 and R'3 are identical or different and represent, independently of one another, hydrogen or C1–C4 alkyl radical;
the distribution agent represents:
  a triazine group,
  wherein the triazine group is a [1,3,5]triazine optionally substituted with:
    an aromatic ring as defined above, or
    a radical XR1(R2), where X represents a nitrogen to form NR1R2, a linear or branched C1–C6 alkyl radical to form alkR1R2, an oxygen to form OR1, or a sulfur to form SR1,
      wherein R1 and R2, which are identical or different, are chosen from among hydrogen; a C1–C8 alkyl radical optionally substituted with one or more radicals which are identical or different; an aromatic ring as defined above; a quinuclidine radical; a pyrrolidinyl radical which is optionally substituted with an alkyl or phenylalkyl radical where alkyl is C1–C4 alkyl; a piperazinyl radical which is optionally substituted with an alkyl, cycloalkyl or phenylalkyl radical; a morpholinyl radical; a pyridyl radical or a piperidyl radical which are optionally substituted with one or more alkyl or phenylalkyl radicals where alkyl is C1–C4 alkyl; an indazolyl radical; a naphthyl radical; a benzotriazole radical; a pyrimidinyl radical optionally substituted with one or more C1–C4 alkyls; and an acenaphthene radical; or
    a radical where X represents N or alkyl, R1 and R2 are as defined above, and R1, R2 and X form a saturated or unsaturated 3- to 6-membered monocyclic or 8- to 10-membered bicyclic radical optionally containing one or two identical or different heteroatoms chosen from N, O or S;
  with the provisos that if X represents a nitrogen and R1 and R2 are identical, then R1 and R2 do not both represent hydrogen or unsubstituted C1–C4 alkyl, and
  if X represents a nitrogen and R1 and R2 are different, then one does not represent hydrogen and the other an unsubstituted C1–C4 alkyl;
or any salts, isomeric forms, racemates, enantiomers and diastereoisomers thereof.

2. The compound of claim 1, wherein one or both of R1 and R2 represents a C1–C8 alkyl radical optionally substituted with one or more radicals which are identical or different, chosen from among:
  an amino radical which is optionally substituted with one or two radicals which are identical or different, chosen from alkyl, hydroxyalkyl, alkoxyalkyl, phenylalkyl, carboxyalkyl, hydroxycarboxyalkyl, acyl, naphthyl, phenyl and alkylphenyl radicals;
  a trialkylammonium radical;
  a hydroxyl radical;
  a C1–C4 alkoxy radical;
  a thioalkoxy radical;
  a trifluoromethyl radical;
  a free, salified, esterified or amidated carboxyl radical;
  a pyrrolidinyl radical optionally substituted with C1–C4 alkyl;
  a piperidyl radical;
  a piperazinyl radical optionally substituted with alkyl or phenylalkyl where alkyl is C1–C4 alkyl;
  a morpholinyl radical;
  a pyridyl radical; and
  a naphthyl radical or phenyl radical optionally substituted with one or more radicals chosen from C1–C4 alkoxy radicals, halogen or an amino radical optionally substituted as defined above.

3. The compound of claim 1, wherein the distribution agent represents
  a triazine group optionally substituted with:
    an aromatic ring as defined in claim 1, or
    a radical XR1(R2), where X represents a nitrogen to form NR1R2, a linear or branched C1–C6 alkyl radical to form alkR1R2, an oxygen to form OR1, or a sulfur to form SR1,
  wherein R1 and R2, which are identical or different, are chosen from:
    hydrogen;
    a C1–C8 alkyl radical optionally substituted with one or more radicals chosen from the radicals amino, alkylamino, dialkylamino, dialkoxyalkylamino, dihydroxyalkylamino, alkoxyalkylamino, hydroxyalkylamino, hydroxycarboxy-alkylamino, trialkylamino, naphthylamino, phenylamino, acylamino, (alkyl)(phenylalkyl)amino, (phenyl)(alkyl)amino, (alkylphenyl)(alkyl)amino, hydroxyl, C1–C4 alkoxy, C1–C4 thioalkoxy, trifluoromethyl, free, salified, esterified or amidated carboxyl, pyrrolidinyl optionally substituted with C1–C4 alkyl, piperidyl, piperazinyl optionally substituted with alkyl or phenylalkyl with alkyl as C1–C4, morpholinyl, pyridyl, naphthyl or phenyl optionally substituted with one or more radicals chosen from the radicals C1–C4 alkoxy, halogen, amino, alkylamino and dialkylamino;

an aromatic ring as defined in claim 1;

a quinuclidine radical;

a pyrrolidinyl radical which is optionally substituted with an alkyl or phenylalkyl radical where alkyl is C1–C4 alkyl;

a piperazinyl radical which is optionally substituted with an alkyl, cycloalkyl or phenylalkyl radical;

a morpholinyl radical;

a pyridyl radical or a piperidyl radical which are optionally substituted with one or more alkyl or phenylalkyl radicals with alkyl is C1–C4 alkyl;

an indazolyl radical;

a naphthyl radical;

a benzotriazole radical;

a pyrimidinyl radical optionally substituted with one or more C1–C4 alkyls; and an acenaphthene radical; or a radical where X represents N or alkyl, R1 and R2 are as defined above, and R1, R2 and X form a radical chosen from the following radicals: piperazinyl optionally substituted with one or more radicals which are identical or different; pyrrolidinyl optionally substituted with C1–C4 alkyl or alkoxy, hydroxyl, acylamino, pyrrolidinylalkyl and pyridyl; 1,2,3,4-tetrahydroisoquinolinyl; diazepine optionally substituted with alkyl or pyrrolidinylalkyl; piperidyl optionally substituted with alkyl, alkoxy or alkoxyalkyl, hydroxyl and cycloalkylalkyl; morpholinyl; imidazolinyl optionally substituted with alkyl, with the provisos that if X represents a nitrogen and R1 and R2 are identical, then R1 and R2 do not both represent hydrogen or unsubstituted C1–C4 alkyl, and if X represents a nitrogen and R1 and R2 are different, then one does not represent hydrogen and the other an unsubstituted C1–C4 alkyl; or a diazine group, wherein the diazine group is optionally substituted with any of the groups defined above for the triazine group;

or any salts, isomeric forms, racemates, enantiomers and diastereoisomers thereof.

4. The compound of claim 1, wherein X in XR1(R2) is nitrogen, and one of R1 and R2 is as defined in claim 1 and the other of R1 and R2 represents hydrogen or C1–C4 alkyl radical optionally substituted with an amino, alkylamino, dialkylamino or phenyl radical; or R1, R2, and the nitrogen atom to which they are attached, form a piperazinyl radical optionally substituted with one or more radicals chosen from alkyl; aminoalkyl; alkylaminoalkyl; dialkylaminoalkyl; phenylalkyl; alkoxyalkyl; hydroxyalkyl; hydroxyalkoxyalkyl; alkoxy; pyrrolidinylalkyl; C3–C8 cycloalkyl; pyrazinyl; pyrimidinyl; pyridyl; furylcarbonyl; furfurylcarbonyl; quinolyl; pyrrolidinyl optionally substituted with C1–C4 alkyl, C1–C4 alkoxy, hydroxyl, acylamino, pyrrolidinylalkyl, or pyridyl; 1,2,3,4-tetrahydroisoquinolinyl; diazepine optionally substituted with alkyl or pyrrolidinylalkyl; piperidyl optionally substituted with alkyl, alkoxy or alkoxyalkyl; hydroxyl; cycloalkylalkyl; morpholinyl; and imidazolinyl optionally substituted with alkyl.

5. The compound of claim 1, wherein the compound corresponds to the following formula:

nitrogen-containing aromatic ring—NR$_3$—distribution agent—NR'$_3$—aromatic ring in which the nitrogen-containing aromatic ring represents:

a quinolinyl or isoquinolinyl radical optionally substituted with at least one radical chosen from among:

N(Ra)(Rb), wherein Ra and Rb are identical or different and represent hydrogen or C1–C4 alkyl radical, and a short-chain C1–C4 alkoxy or alkyl group, a quinolinyl radical possessing a nitrogen atom in quaternary form, or a pyridinyl radical;

or wherein the nitrogen-containing ring is replaced by a benzimidinyl radical;

the aromatic ring represents:

a quinolinyl radical optionally substituted with at least one radical chosen from among:

N(Ra)(Rb), wherein Ra and Rb are identical or different and represent hydrogen or C1–C4 alkyl radical, and a short-chain C1–C4 alkoxy or alkyl group, a quinolinyl radical possessing a nitrogen atom in quaternary form, a benzamidinyl radical, a pyridinyl radical, a phenyl ring optionally substituted with a halogen chosen from iodine, bromine or fluorine, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group, C1–C4 dialkylamino group in which the alkyl portions together form a C3–C8 ring, nitro group, C1–C4 alkyleneamino group, or C2–C4 alkenyleneamino group, or a mono- or bi- or tricyclic heterocyclic ring comprising 0 to 2 heteroatoms per ring wherein at least one heteroatom is present in at least one ring that is optionally substituted with one or more C1–C4 alkyl groups, C1–C4 alkylene, or C2–C4 alkenylene groups;

R3 and R'3 are identical or different and represent, independently of one another, hydrogen or C1–C4 alkyl radical;

the distribution agent represents:

a triazine group, wherein the triazine group is a [1,3,5]triazine optionally substituted with:

a radical XR1(R2), where X represents a nitrogen to form NR1R2, a linear or branched C1–C6 alkyl radical to form alkR1R2, an oxygen to form OR1, or a sulfur to form SR1, wherein R1 and R2, which are identical or different, are chosen from among hydrogen; C1–C8 alkyl optionally substituted with a radical chosen from amino, alkylamino, dialkylamino, (phenyl)(alkyl) amino, (alkylphenyl)(alkyl)-amino, C1–C4 alkoxy, C1–C4 thioalkoxy, trifluoromethyl, pyrrolidiny, piperidyl, piperazinyl, morpholinyl, pyridyl and phenyl; an aromatic ring as defined in claim 1, a quinuclidine radical; a pyrrolidinyl, piperazinyl, morpholinyl, pyridyl or a piperidyl radical optionally substituted with C1–C4 alkyl; or a radical where X represents N or alkyl, R1 and R2 are as defined above, and R1, R2 and X form a saturated or unsaturated 3- to 6-membered monocyclic or 8- to 10-membered bicyclic radical optionally containing one or two identical or different heteroatoms chosen from N, O or S;

with the provisos that if X represents a nitrogen and R1 and R2 are identical, then R1 and R2 do not both represent hydrogen or unsubstituted C1–C4 alkyl, and if X represents a nitrogen and R1 and R2 are different, then one does not represent hydrogen and the other an unsubstituted C1–C4 alkyl;

or any salts, isomeric forms, racemates, enantiomers and diastereoisomers thereof.

6. The compound of claim 1, wherein the distribution agent represents:

a [1,3,5]triazine optionally substituted with a radical XR1(R2) where X represents a nitrogen to form NR1R2, an oxygen to form OR1, or a sulfur to form SR1, wherein R2 and R2, which are identical or different, are chosen from among:

hydrogen,

C1–C8 alkyl optionally substituted with a radical chosen from amino, alkylamino, dialkylamino, (phenyl) (alkyl)amino, (alkylphenyl)(alkyl)-amino, C1–C4 alkoxy, pyrrolidinyl, pyridyl, and phenyl, an aromatic ring as defined in claim 1;

a quinuclidine radical;

a pyrrolidinyl radical; and a piperidyl radical optionally substituted with C1–C4 alkyl, or a radical where X represents N, R1 and R2 are as defined above, and R1, R2, and X form a piperazinyl, piperidyl, pyrrolidinyl, morpholinyl or thiomorpholinyl radical, with the provisos that if X represents a nitrogen and R1 and R2 are identical, then R1 and R2 do not both represent hydrogen or unsubstituted C1–C4 alkyl, and if X represents a nitrogen and R1 and R2 are different, then one does not represent hydrogen and the other an unsubstituted C1–C4 alkyl;

or any salts, isomeric forms, racemates, enantiomers and diastereoisomers thereof.

7. The compound of claim 1, corresponding to formula (I) below:

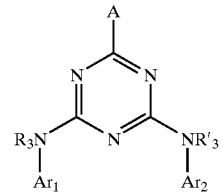

wherein:

A represents a radical XR1(R2) in which X represents a nitrogen, oxygen, or sulfur atom or a C1–C6 alkyl radical in order to form one of the following radicals:
NR1R2, wherein R1 and R2 are identical or different and are chosen from:
hydrogen;
C1–C8 alkyl optionally substituted with one or more radicals which are identical or different;
an aromatic ring as defined in claim 1;
a quinuclidine radical;
a pyrrolidinyl radical which is itself optionally substituted with alkyl or phenylalkyl radical with alkyl as C1–C4;
a piperazinyl radical which is itself optionally substituted with an alkyl, cycloalkyl or phenylalkyl radical;
a morpholinyl radical;
a pyridyl radical or a piperidyl radical which is optionally substituted with one or more alkyl or phenylalkyl radicals with C1–C4 alkyl;
an indazolyl radical; a naphthyl radical; a benzotriazole radical; a pyrimidinyl radical optionally substituted with one or more alkyls with alkyl as C1–C4; and
an acenaphthene radical; or
a radical where X represents N or alkyl, R1 and R2 are as defined above, and R1, R2 and X form a saturated or unsaturated 3- to 6-membered monocyclic or 8- to 10-membered bicyclic radical optionally containing one or two identical or different heteroatoms chosen from N, O or S; with the provisos that if X represents a nitrogen and R1 and R2 are identical, then R1 and R2 do not both represent hydrogen or unsubstituted C1–C4 alkyl, and
if X represents a nitrogen and R1 and R2 are different, then one does not represent hydrogen and the other an unsubstituted C1–C4 alkyl;
a group OR1 or SR1, wherein R1 has the same meaning as above, with the proviso that R1 does not represent hydrogen or unsubstituted C1–C4 alkyl, or an alkyl group containing from 1 to 6 carbon atoms, substituted with R1 and R2 as defined above;

R3 and R'3, which are identical or different, represent independently of one another hydrogen or a C1–C4 alkyl group;

Ar$_1$ and Ar$_2$, if identical, represent:
a quinolinyl radical optionally substituted with at least one group N(Ra)(Rb) in which Ra and Rb, which are identical or different, represent hydrogen, a C1–C4 alkyl radical, or a short-chain alkoxy or alkyl group containing 1 to 4 carbon atoms, or
a quinolinyl radical possessing a nitrogen atom in quaternary form or a benzamidinyl radical, or a pyridinyl radical attached at the 4-position or fused with an aryl or heteroaryl group optionally substituted with a C1–C4 alkyl group; and Ar₁ and Ar₂, when different:
both represent one of the radicals recited above for Ar₁ and Ar₂, or Ar₁ represents one of the above radicals and Ar₂ represents a phenyl ring optionally substituted with a halogen chosen from iodine, bromine or fluorine, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group, nitro group, C1–C4 alkyleneamino group, or C2–C4 alkenyleneamino group, or a piperazinyl radical optionally substituted with a C1–C4 alkyl radical, or a mono-, bi-, or tricyclic heterocyclic ring comprising 0 to 2 heteroatoms per ring provided that at least one heteroatom is present in at least one ring that is optionally substituted with one or more C1–C4 alkyl groups, C1–C4 alkylene, or C2–C4 alkenylene groups;

or any salts, isomeric forms, racemates, enantiomers and diastereoisomers thereof.

8. The compound of claim 7, wherein one or both of R1 and R2 represents a C1–C8 alkyl radical optionally substituted with one or more radicals which are identical or different, wherein these radicals are chosen from an amino radical optionally substituted with one or two radicals which are identical or different, chosen from alkyl, hydroxyalkyl, alkoxyalkyl, phenylalkyl, carboxyalkyl, hydroxycarboxyalkyl, acyl, naphthyl, phenyl and alkylphenyl radicals; trialkylammonium radical; hydroxyl radical; alkoxy radical; thioalkoxy radical; trifluoromethyl radical; free, salified, esterified or amidated carboxyl radical; pyrrolidinyl radical optionally substituted with C1–C4 alkyl; piperidyl radical; piperazinyl radical optionally substituted with alkyl or phenylalkyl where alkyl is C1–C4 alkyl; morpholinyl radical; pyridyl radical; and naphthyl radical or phenyl radical optionally substituted with one or more radicals chosen from C1–C4 alkoxy radicals, halogen or amino radical optionally substituted as defined above.

9. The compound of claim 1, wherein X in XR1(R2) represents N, one of R1 and R2 represents a hydrogen atom and the other of R1 and R2 is as defined in claim 1; or R1 and R2, together with the nitrogen atom to which they are attached, form a piperazinyl, pyrrolidinyl, piperidyl, morpholinyl, thiomorpholinyl, imidazolinyl, diazepine, or 1,2,3,4-tetrahydroisoquinoline radical, all these radicals being optionally substituted with one or more radicals.

10. The compound of claim 7, wherein A represents an aromatic ring as defined above or a radical XR1(R2) in which X represents a nitrogen to form NR1R2, a linear or branched C1–C6 alkyl radical to form alkR1R2, an oxygen to form OR1, or a sulfur to form SR1, wherein R1 and R2, which are identical or different, are chosen from:
hydrogen;
C1–C8 alkyl optionally substituted with one or more radicals chosen from amino, alkylamino, dialkylamino, dialkoxyalkylamino, dihydroxyalkylamino, alkoxyalkylamino, hydroxyalkylamino, hydroxycarboxyalkylamino, trialkylammonium, naphthylamino, phenylamino, acylamino, (alkyl)(phenylalkyl)amino, (phenyl)(alkyl)amino, (alkylphenyl)(alkyl)amino, hydroxyl, C1–C4 alkoxy, C1–C4 thioalkoxy, trifluoromethyl, free, salified, esterified or amidated carboxyl, pyrrolidinyl optionally substituted with C1–C4 alkyl, piperidyl, piperazinyl optionally substituted with alkyl or phenylalkyl with alkyl as C1–C4, morpholinyl, pyridyl, naphthyl or phenyl optionally substituted with one or more radicals chosen from the radicals C1–C4 alkoxy, halogen, amino, alkylamino and dialkylamino;

an aromatic ring as defined in claim 7;
a quinuclidine radical;
a pyrrolidinyl radical which is itself optionally substituted with an alkyl or phenylalkyl radical with alkyl as C1–C4;
a piperazinyl radical which is itself optionally substituted with an alkyl, cycloalkyl or phenylalkyl radical;
a morpholinyl radical;
a pyridyl radical or a piperidyl radical which are optionally substituted with one or more alkyl or phenylalkyl radicals with C1–C4 alkyl;
an indazolyl radical;
a naphthyl radical,
a benzotriazole radical;
a pyrimidinyl radical optionally substituted with one or more C1–C4 alkyl radicals; and
an acenaphthene radical; or R1 and R2, together with the X to which they are attached, form a radical chosen from the following radicals: piperazinyl optionally substituted with one or more radicals which are identical or different; pyrrolidinyl optionally substituted with C1–C4 alkyl or alkoxy, hydroxyl, acylamino, pyrrolidinylalkyl and pyridyl;

1,2,3,4-tetrahydroisoquinolinyl; diazepine optionally substituted with alkyl or pyrrolidinylalkyl; piperidyl optionally substituted with alkyl, alkoxy or alkoxyalkyl, hydroxyl and cycloalkylalkyl; morpholinyl; and imidazolinyl optionally substituted with alkyl;

with the provisos that if X represents a nitrogen and R1 and R2 are identical, then R1 and R2 do not both represent hydrogen or unsubstituted C1–C4 alkyl, and if X represents a nitrogen and R1 and R2 are different, then one does not represent hydrogen and the other an unsubstituted C1–C4 alkyl.

11. The compound of claim 7, wherein X in XR1(R2) represents N, and one of R1 and R2 represents a hydrogen or C1–C4 alkyl radical optionally substituted with an amino, alkylamino, dialkylamino or phenyl radical, and the other of R1 and R2 is as defined in claim 7; or R1, R2, and the nitrogen atom to which they are attached, form a piperazinyl radical optionally substituted with one or more radicals chosen from alkyl, aminoalkyl, alkylaminoalkyl, dialkylaminoalkyl, phenylalkyl, alkoxyalkyl, hydroxyalkyl, hydroxyalkoxyalkyl, alkoxy, pyrrolidinylalkyl, C3–C8 cycloalkyl, pyrazinyl, pyrimidinyl, pyridyl, furylcarbonyl, furfurylcarbonyl, quinolyl, pyrrolidinyl optionally substituted with C1–C4 alkyl or alkoxy, hydroxyl, acylamino, pyrrolidinylalkyl, pyridyl, 1,2,3,4-tetrahydroiso-quinolinyl, diazepine optionally substituted with alkyl or pyrrolidinylalkyl, piperidyl optionally substituted with alkyl, alkoxy or alkoxyalkyl; hydroxyl; cycloalkylalkyl; morpholinyl; and imidazolinyl optionally substituted with alkyl.

12. The compound of claim 7, wherein the compounds correspond to formula (I) below:

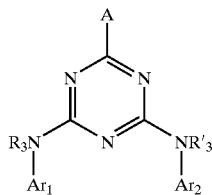

wherein:
A represents a radical XR1(R2) in which X represents a nitrogen, oxygen or sulfur atom, or a C1–C6 alkyl radical, to form one of the following radicals:
NR1R2, wherein R1 and R2, which are identical or different, are chosen from a hydrogen atom; C1–C8 alkyl optionally substituted with an amino, alkylamino, dialkylamino, (phenyl)(alkyl)amino, (alkylphenyl)(alkyl)amino, C1–C4 alkoxy, C1–C4 thioalkoxy, trifluoromethyl, pyrrolidinyl, piperidyl, piperazinyl, morpholinyl, pyridyl or phenyl; an aromatic ring as defined in claim 7; a quinuclidine radical; and a pyrrolidinyl, piperazinyl, morpholinyl, pyridyl, or piperidyl radical optionally substituted with C1–C4 alkyl; or
when X is N or alkyl, R1 and R2, together with the X to which they are attached, form a saturated or unsaturated 3- to 6-membered monocyclic or 8- to 10-membered bicyclic radical optionally containing one or two heteroatoms, which are identical or different, chosen from N, O or S,
with the provisos that if X represents a nitrogen and R1 and R2 are identical, then R1 and R2 do not both represent hydrogen or unsubstituted C1–C4 alkyl, and
if X represents a nitrogen and R1 and R2 are different, then one does not represent hydrogen and the other an unsubstituted C1–C4 alkyl;
a group OR1 or SR1 in which R1 has the same meaning as above, with the proviso that R1 does not represent hydrogen or unsubstituted C1–C4 alkyl; or
an alkyl group containing from 1 to 6 carbon atoms, substituted with R1 and R2 as defined above;
R3 and R'3, which are identical or different, represent independently of one another hydrogen or a C1–C4 alkyl group;
$Ar_1$ and $Ar_2$, when identical, represent
a quinolinyl radical optionally substituted with at least one group N(Ra)(Rb) in which Ra and Rb, which are identical or different, represent hydrogen, a C1–C4 alkyl radical, or a short-chain alkoxy or alkyl group containing 1 to 4 carbon atoms,
a quinolinyl radical possessing a nitrogen atom in quaternary form,
a benzamidinyl radical, or
a pyridinyl radical attached at the 4-position or fused with an aryl or heteroaryl group optionally substituted with a C1–C4 alkyl group; and
$Ar_1$ and $Ar_2$, when different:
both represent one of the radicals recited above for $Ar_1$ and $Ar_2$, or
$Ar_1$ represents one of the above recited radicals and $Ar_2$ represents
a phenyl ring optionally substituted with a halogen chosen from iodine, bromine or fluorine, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group for each alkyl group, nitro group, C1–C4 alkyleneamino group, C2–C4 alkenyleneamino group, or a piperazinyl radical optionally substituted with a C1–C4 alkyl radical,
a mono- or bi- or tricyclic heterocyclic ring comprising 0 to 2 heteroatoms per ring provided that at least one heteroatom is present in at least one ring that is optionally substituted with one or more C1–C4 alkyl groups, C1–C4 alkylene, or C2–C4 alkenylene groups;
or any salts, isomeric forms, racemates, enantiomers and diastereoisomers thereof.

13. The compound of claim 7, wherein the compound corresponds to formula (I) below:

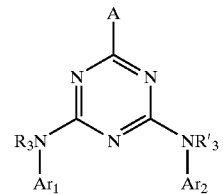

wherein:
A represents a radical XR1(R2) in which X represents a nitrogen, oxygen or sulfur atom, or a C1–C6 alkyl radical, to form one of the following radicals:
NR1R2, wherein R1 and R2, which are identical or different, are chosen from hydrogen; C1–C8 alkyl optionally substituted with a radical amino, alkylamino, dialkylamino, (phenyl)(alkyl)amino, (alkylphenyl)(alkyl)amino, C1–C4 alkoxy, C1–C4 thioalkoxy, trifluoromethyl, pyrrolidinyl, piperidyl, piperazinyl, morpholinyl, pyridyl or phenyl; an aromatic ring as defined in claim 7; a quinuclidine radical; and a pyrrolidinyl, piperazinyl, morpholinyl, pyridyl or piperidyl radical optionally substituted with C1–C4 alkyl; or
R1 and R2, together with the X to which they are attached, form a saturated or unsaturated 3- to 6-membered monocyclic or 8- to 10-membered bicyclic radical optionally containing one or two heteroatoms, which are identical or different, chosen from N, O or S;
with the provisos that if X represents a nitrogen and R1 and R2 are identical, then R1 and R2 do not both represent hydrogen or unsubstituted C1–C4 alkyl, and
if X represents a nitrogen and R1 and R2 are different, then one does not represent hydrogen and the other an unsubstituted C1–C4 alkyl;
a group OR1 or SR1 in which R1 has the same meaning as above, with the proviso that R1 does not represent hydrogen or unsubstituted C1–C4 alkyl; or
an alkyl group containing from 1 to 6 carbon atoms, substituted with R1 and R2 as defined above;
R3 and R'3, which are identical or different, represent independently of one another hydrogen or a C1–C4 alkyl group;
$Ar_1$ and $Ar_2$, when identical, represent
a quinolinyl radical optionally substituted with at least one group N(Ra)(Rb) in which Ra and Rb, which are identical or different, represent hydrogen, a C1–C4 alkyl radical, or a short-chain alkoxy or alkyl group containing 1 to 4 carbon atoms,
a quinolinyl radical possessing a nitrogen atom in quaternary form,
a benzamidinyl radical, or
a pyridinyl radical attached at the 4-position or fused with an aryl or heteroaryl group optionally substituted with a C1–C4 alkyl group; and $Ar_1$ and $Ar_2$, when different:
both represent one of the radicals recited above for $Ar_1$ and $Ar_2$, or
$Ar_1$ represents one of the above recited radicals and $Ar_2$ represents
a phenyl ring optionally substituted with a halogen chosen from iodine, bromine or fluorine, C1–C4 alkoxy group, cyano group, carbonylamino group optionally substituted with one or more C1–C4 alkyl groups, guanyl group, C1–C4 alkylthio group, amino group, C1–C4 alkylamino group, C1–C4 dialkylamino group for each alkyl group, nitro group, C1–C4 alkyleneamino group, C2–C4 alkenyleneamino group, or a piperazinyl radical optionally substituted with a C1–C4 alkyl radical,
a mono- or bi- or tricyclic heterocyclic ring comprising 0 to 2 heteroatoms per ring provided that at least one heteroatom is present in at least one ring that is optionally substituted with one or more C1–C4 alkyl groups, C1–C4 alkylene, or C2–C4 alkenylene groups; or any salts, isomeric forms, racemates, enantiomers and diastereoisomers thereof.

14. The compound of claim 7, wherein
A represents a radical XR1(R2) in which X represents nitrogen to form NR1R2, an oxygen to form OR1, or a sulfur to form SR1, to form one of the following radicals:
NR1R2, wherein R1 and R2, which are identical or different, are chosen from hydrogen; C1–C8 alkyl optionally substituted with a amino, alkylamino, dialkylamino, (phenyl)(alkyl)amino, (alkylphenyl)(alkyl)amino, C1–C4 alkoxy, pyrrolidinyl, pyridyl or phenyl radical; an aromatic ring as defined in claim 7; a quinuclidine radical, a pyrrolidinyl radical or a piperidyl radical optionally substituted with C1–C4 alkyl; or
R1 and R2, together with the X to which they are attached, form a piperazinyl, piperidyl, pyrrolidinyl, morpholinyl, or thiomorpholinyl radical, with the provisos that if X represents a nitrogen and R1 and R2 are identical, then R1 and R2 do not both represent hydrogen or unsubstituted C1–C4 alkyl, and if X represents a nitrogen and R1 and R2 are different, then one does not represent hydrogen and the other an unsubstituted C1–C4 alkyl;
a group OR1 or SR1 in which R1 has the same meaning as above, with the proviso that R1 does not represent hydrogen or unsubstituted C1–C4 alkyl;
or any salts, isomeric forms, racemates, enantiomers and diastereoisomers thereof.

15. The compound of claim 7, wherein A represents NR1R2, and one of R1 and R2 represents hydrogen and the other of R1 and R2 is as defined in claim 7, or R1 and R2, together with the nitrogen atom to which they are attached, form a piperazinyl, pyrrolidinyl, piperidyl or morpholinyl radical.

16. The compound of claim 7, wherein $Ar_1$ and $Ar_2$ represent a group chosen from: 4-amino-, 4-methylamino-, 4-dimethylamino-quinolyl or -quinolinium in which the quinolinium ring is optionally substituted with a methyl group; or a phenyl optionally substituted with one or more halogen atoms chosen from iodine, bromine or fluorine.

17. The compound of claim 7, wherein A represents: an amino radical substituted with a radical chosen from the following groups: 4-amino-, 4-methylamino-, or 4-dimethylamino-quinolyl or -quinolinium in which the quinolinium ring is optionally substituted with a methyl; pyridyl; phenyl optionally substituted with one or more halogen atoms; piperazinyl or alkylpiperazinyl; C1–C4 alkyl substituted with an amino, alkylamino or dialkylamino; (phenyl)(alkyl)amino; (alkylphenyl)(alkyl)amino, C2–C4 alkoxy, with a pyrrolidinyl radical or with a phenyl radical, in which radicals the alkyl groups possess 1 to 4 carbon atoms; a pyrrolidinyl radical; a piperidyl radical optionally substituted with a C1–C4 alkyl radical; or a quinuclidine radical or a pyrrolidinyl radical, a morpholino radical or a piperazinyl radical optionally substituted with a C1–C4 alkyl radical or a radical O-phenyl, O-pyridyl or O-alkyl substituted with an amino, alkylamino or dialkylamino radical.

18. The compound of claim 7, wherein $Ar_1$ and $Ar_2$ are identical, and $Ar_1$ and $Ar_2$ represent a group chosen from 4-amino-, 4-methylamino-, or 4-dimethylamino-quinolyl or -quinolinium in which the quinolinium ring is optionally substituted with a methyl group.

19. The compound of claim 7, wherein $Ar_1$ and $Ar_2$ are different, and
$Ar_1$ represents:
a quinolinyl radical substituted with at least one group N(Ra)(Rb) in which Ra and Rb, which are identical or different, represent hydrogen or a C1–C4 alkyl radical or a short-chain alkoxy or alkyl group containing 1 to 4 carbon atoms,
a quinolinyl radical possessing a nitrogen atom in quaternary form
a benzamidinyl radical, except if A represents diethylamine, hydrogen, or an amine group, then $Ar_1$ is not benzamidine, or
a pyridinyl radical attached at the 4-position or fused with an aryl or heteroaryl group; and
$Ar_2$ represents:
a ring as defined above, or
a phenyl ring optionally substituted with a halogen chosen from iodine, bromine or fluorine, methoxy, cyano, carbonylamino, guanyl, methylthio, amino, methylamino, dimethylamino, morpholine, C1–C4 alkyleneamino or C2–C4 alkenyleneamino group, or
a quinoline, benzimidazole, indole, benzothiophene, benzofuran, benzothiazole, benzoxazole, carbazole, quinazoline or quinoxaline ring optionally substituted with one or more C1–C4 alkyl groups, C1–C4 alkylene, or C2–C4 alkenylene groups.

20. The compound of claim 7, wherein A represents an amino radical substituted with a radical chosen from among: 4-amino-, 4-methylamino-, or 4-dimethylamino-quinolinyl or -quinolinium radicals wherein the quinolinium ring is optionally substituted with a methyl group; C1–C4 alkyl radical substituted with an amino, alkylamino, dialkylamino, (phenyl)(alkyl)amino, (alkylphenyl)(alkyl)amino, pyrrolidinyl or pyridyl radical; or the quinuclidine radical.

21. The compound of claim 7, wherein A represents either an amino radical substituted with a pyridyl radical; a phenyl radical optionally substituted with a piperazinyl or alkylpiperazinyl radical; a piperidyl radical optionally substituted with a C1–C4 alkyl radical; or a piperazinyl radical optionally substituted with a C1–C4 alkyl radical.

22. The compound of claim 7, wherein A represents O-phenyl, O-pyridyl, or O-alkyl substituted with an amino, alkylamino or dialkylamino radical.

23. The compound of claim 7, wherein A represents a radical O(or S)-aromatic ring or a radical O(or S)-alkyl with alkyl optionally substituted.

24. The compound of claim 1, wherein the compound is:
- 2,4-bis(4-dimethylamino-2-methylquinolin-6-yl)amino-6-(3-dimethylaminopropyl)amino-[1,3,5]triazine,
- 2,4,6-tris(4-amino-2-methylquinolin-6-yl)amino-[1,3,5]triazine,
- 2,4-bis(4-amino-2-methylquinolin-6-yl)amino-6-(4-dimethylamino-2-methylquinolin-6-yl)amino-[1,3,5]triazine,
- 2,4-bis(4-amino-2-methylquinolin-6-yl)amino-6-(quinuclidin-3-yl)amino-[1,3,5]-triazine,
- 2,4-bis(4-dimethylamino-2-methylquinolin-6-yl)amino-6-(1-methylpiperidin-4-yl)-[1,3,5]triazine,
- 2,4-bis(4-dimethylamino-2-methylquinolin-6-yl)amino-6-(1-methylpiperazin-4-yl)-[1,3,5]triazine,
- 2,4-bis(4-dimethylamino-2-methylquinolin-6-yl)amino-6-(pyridin-4-yl)methylamino-[1,3,5]triazine,
- 2,4-bis(4-amino-2-methylquinolin-6-yl)amino-6-phenoxy-[1,3,5]triazine,
- 2,4-bis(4-amino-2-methylquinolin-6-yl)amino-6-(3-dimethylaminopropyl)oxy-[1,3,5]triazine,
- 2,4-bis(4-amino-2-methylquinolin-6-yl)amino-6-(pyridin-4-yl)oxy-[1,3,5]triazine, or
- 2,4-bis(4-amino-2-methylquinolin-6-yl)amino-6-(phenylmethyl)oxy-[1,3,5]triazine.

25. The compound of claim 1, wherein the compound is:
- 2,4-bis(4-dimethylamino-2-methylquinolin-6-yl)amino-6-(3-dimethylaminopropyl)amino-[1,3,5]triazine,
- 2,4,6-tris(4-amino-2-methylquinolin-6-yl)amino-[1,3,5]triazine,
- 2,4-bis(4-amino-2-methylquinolin-6-yl)amino-6-(4-dimethylamino-2-methylquinolin-6-yl)amino-[1,3,5]triazine,
- 2,4-bis(4-dimethylamino-2-methylquinolin-6-yl)amino-6-(1-methylpiperazin-4-yl)-[1,3,5]triazine,
- 2,4-bis(4-dimethylamino-2-methylquinolin-6-yl)amino-6-(pyridin-4-yl)oxy-[1,3,5]triazine,
- 2,4-bis(4-amino-2-methylquinolin-6-yl)amino-6-(quinolin-2-yl)thio-[1,3,5]triazine,
- 2,4-bis(4-dimethylamino-2-methylquinolin-6-yl)amino-6-phenyl-[1,3,5]triazine,
- 2,4-bis(4-dimethylamino-2-methylquinolin-6-yl)amino-6-[1-(2-dipropylaminoethyl)piperazin-4-yl]-[1,3,5]triazine,
- 2,4-bis(4-dimethylamino-2-methylquinolin-6-yl)amino-6-{[1-2-(2-hydroxyethyl)oxyethyl]piperazin-4-yl}-[1,3,5]triazine,
- 2,4-bis(4-dimethylamino-2-methylquinolin-6-yl)amino-6-[2(S)-(pyrrolidin-1-yl)methylpyrrolidin-1-yl]-[1,3,5]triazine,
- 2,4-bis(4-dimethylamino-2-methylquinolin-6-yl)amino-6-(quinolin-2-yl)thio-[1,3,5]triazine,
- 2,4-bis(4-dimethylamino-2-methylquinolin-6-yl)amino-6-(1-methylhomopiperazin-4-yl)-[1,3,5]triazine,
- 2,4-bis(4-dimethylamino-2-methylquinolin-6-yl)amino-6-[1-(3-dimethylaminopropyl)piperazin-4-yl]-[1,3,5]triazine,
- 2,4-bis(4-dimethylamino-2-methylquinolin-6-yl)amino-6-[N-(1-methylpiperidin-4-yl)-N-methylamino]-[1,3,5]triazine,
- 2,4-bis(4-dimethylamino-2-methylquinolin-6-yl)amino-6-{1-[3-(pyrrolidin-1-yl)propylhomopiperazin-4-yl)-[1,3,5]triazine, or
- 2,4-bis(4-dimethylamino-2-methylquinolin-6-yl)amino-6-[1-(pyridin-4-yl)piperazin-4-yl]-[1,3,5]triazine.

26. The compound of claim 1, wherein the compound is:
- 2,4-bis(4-dimethylamino-2-methylquinolin-6-yl)amino-6-(1-methylpiperazin-4-yl)-[1,3,5]triazine,
- 2,4-bis(4-dimethylamino-2-methylquinolin-6-yl)amino-6-(quinolin-2-yl)thio-[1,3,5]triazine,
- 2,4-bis(4-dimethylamino-2-methylquinolin-6-yl)amino-6-(1-methylhomopiperazin-4-yl)-[1,3,5]triazine,
- 2,4-bis(4-dimethylamino-2-methylquinolin-6-yl)amino-6-[1-(3-dimethylaminopropyl)piperazin-4-yl]-[1,3,5]triazine,
- 2,4-bis(4-dimethylamino-2-methylquinolin-6-yl)amino-6-[N-(1-methylpiperidin-4-yl)-N-methylamino]-[1,3,5]triazine,
- 2,4-bis(4-dimethylamino-2-methylquinolin-6-yl)amino-6-{1-[3-(pyrrolidin-1-yl)propylhomopiperazin-4-yl)-[1,3,5]triazine, or
- 2,4-bis(4-dimethylamino-2-methylquinolin-6-yl)amino-6-[1-(pyridin-4-yl)piperazin-4-yl]-[1,3,5]triazine.

27. A compound selected from the group consisting of:
- N-(4-amino-2-methyl-quinolin-6-yl)-N'-(2-chloro-phenyl)-N"-(4-dimethylamino-2-methyl-quinolin-6-yl)-[1,3,5]triazine-2,4,6-triamine;
- N-(4-amino-2-methyl-quinolin-6-yl)-N'-(2-chloro-phenyl)-N"-pyridin-4-yl-[1,3,5]triazine-2,4,6-triamine;
- N-(4-amino-2-methyl-quinolin-6-yl)-N'-(2-chloro-phenyl)-N"-(2-dimethylamino-ethyl)-[1,3,5]triazine-2,4,6-triamine;
- N-(4-amino-2-methyl-quinolin-6-yl)-N'-(2-chloro-phenyl)-N"-(3-dimethylamino-propyl)-[1,3,5]triazine-2,4,6-triamine;
- N-(4-amino-2-methyl-quinolin-6-yl)-N'-(2-chloro-phenyl)-N"-(1-methyl-piperidin-4-yl)-[1,3,5]triazine-2,4,6-triamine;
- N*6*-[4-(2-chloro-phenylamino)-6-(4-methyl-piperazin-1-yl)-[1,3,5]triazin-2-yl]-2-methyl-quinoline-4,6-diamine;
- N,N'-bis-(4-amino-2-methyl-quinolin-6-yl)-N"-(4-chloro-phenyl)-[1,3,5]triazine-2,4,6-triamine;
- N,N'-2,4-bis-(4-amino-2-methyl-quinolin-6-yl)amino-6-(4-chloro-phenoxy)-[1,3,5]triazine; and
- N,N'-2,4-bis-(4-amino-2-methyl-quinolin-6-yl)amino-6-(4-chloro-phenyl)thio-[1,3,5]triazine.

28. A pharmaceutical composition for human use comprising a compound of claim 1 and one or more pharmaceutically acceptable excipients.

29. A pharmaceutical composition comprising, as active ingredient, one or more compounds according to claim 1.

30. A pharmaceutical composition comprising, as active ingredient, one or more compounds according to claim 24.

31. A pharmaceutical composition comprising, as active ingredient, one or more compounds according to claim 25.

32. A pharmaceutical composition comprising, as active ingredient, one or more compounds according to claim 26.

33. A therapeutic combination comprising the administration of a therapeutically effective amount of compound of claim 1, and the administration of radiation.

34. The therapeutic combination of claim 33, wherein the compound of claim 1 and radiation are administered simultaneously, separately or sequentially.

* * * * *